United States Patent
Horning et al.

(10) Patent No.: US 10,139,393 B2
(45) Date of Patent: *Nov. 27, 2018

(54) SYSTEMS AND METHODS FOR MONITORING OF BLOOD LACTATE AND TARGETING OF BLOOD LACTATE VIA NUTRITIONAL SUPPORT

(71) Applicant: Run Them Sweet LLC, San Francisco, CA (US)

(72) Inventors: Michael A. Horning, San Francisco, CA (US); George A. Brooks, Seattle, WA (US)

(73) Assignee: RUN THEM SWEET LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,755

(22) Filed: Nov. 3, 2017

(65) Prior Publication Data
US 2018/0139999 A1  May 24, 2018

Related U.S. Application Data

(63) Continuation of application No. 15/728,880, filed on Oct. 10, 2017, now Pat. No. 10,088,470, which is a continuation of application No. 15/408,152, filed on Jan. 17, 2017, which is a continuation of application No. 14/941,197, filed on Nov. 13, 2015, now Pat. No. 9,687,011, which is a continuation of application No. 14/043,703, filed on Oct. 1, 2013, now Pat. No. 9,232,815, application No. 15/802,755, which is a continuation of application No. 15/408,152, which is a continuation of application No. 14/941,197, which is a continuation of application No. 14/043,703, application No. 15/802,755, which is a continuation-in-part of application No. 13/903,929, filed on May 28, 2013, now Pat. No. 9,808,031.

(60) Provisional application No. 61/795,819, filed on Oct. 25, 2012.

(51) Int. Cl.
| | |
|---|---|
| *G01N 33/50* | (2006.01) |
| *G01N 33/66* | (2006.01) |
| *A61K 31/225* | (2006.01) |
| *A61K 31/223* | (2006.01) |
| *A23L 33/00* | (2016.01) |
| *A61K 31/19* | (2006.01) |

(52) U.S. Cl.
CPC .............. *G01N 33/50* (2013.01); *A23L 33/30* (2016.08); *A61K 31/223* (2013.01); *A61K 31/225* (2013.01); *G01N 33/66* (2013.01); *A61K 31/19* (2013.01); *G01N 2800/02* (2013.01); *G01N 2800/52* (2013.01); *G01N 2800/7066* (2013.01); *G01N 2800/7071* (2013.01)

(58) Field of Classification Search
None
See application file for complete search history.

(56) References Cited

U.S. PATENT DOCUMENTS

2008/0275136 A1  11/2008 Grynberg
2009/0285909 A1  11/2009 Leverve

OTHER PUBLICATIONS

Zhao, Qing-Jv, Xue-Guang Zhang, and Le-Xin Wang. "Mild hypothermia therapy reduces blood glucose and lactate and improves neurologic outcomes in patients with severe traumatic brain injury." Journal of critical care 26.3 (2011): 311-315 (Year: 2011).*
Bakker, Jan, Maarten WN Nijsten, and Tim C. Jansen. "Clinical use of lactate monitoring in critically ill patients." Annals of intensive care 3.1 (2013): 12. (Year: 2013).*
Vizzini, Angela, and Jaime Aranda-Michel. "Nutritional support in head injury." Nutrition 27.2 (2011): 129-132. (Year: 2011).*
Cureton, E. A Different View of Lactate. Journal of Surgical Research, 159, 468, 2010.
Meirelles, C. Enteral or Parenteral Nutrition in Traumatic Brain Injury. Nutr Hosp, 25(5), 1120, 2011.
Berthet, C. Neuroprotective role of lactate after cerebral ischemia, J Cereb Blood Flow Metab. Nov. 2009;29(11)1780-9.
Holloway, R. Effect of lactate therapy upon cognitive deficits after traumatic brain injury in the rat. Acta Neurochir (Wien). 2007;149(9):919-27; discussion 927. Epub Jul. 30, 2007.
King, P. Intravenous lactate prevents cerebral dysfunction during hypoglycaemia in insulin-dependent diabetes mellitus.
Berger, C. Neurochemical monitoring of glycerol therapy in patients with ischemic brain edema.Stroke. Feb. 2005;36(2):e4-6. Epub Dec. 23, 2004.

* cited by examiner

*Primary Examiner* — Robert J Yamasaki
(74) *Attorney, Agent, or Firm* — Robert H Lee

(57) ABSTRACT

Systems, techniques and methods for estimating the metabolic state or flux, e.g., the body energy state ("BES") of a patient, are disclosed. The BES provides a deep insight into the nutritional needs of the patient, thus allowing for a sort of exquisite glycemic control with regard to the patient. The invention discloses systems and methods for estimating fractional gluconeogenesis. The invention also discloses systems and methods for estimating and targeting patient blood lactate concentration, both as a target itself and as an intermediate step to estimating and targeting patient fractional gluconeogenesis glucose production. Nutritional support methods and formulations are also disclosed. The invention is suitable for any sort of patient, including those who are injured, such as with traumatic brain injury, ill, or have other conditions that stress the metabolic system.

18 Claims, 10 Drawing Sheets

SYSTEMS AND METHODS FOR MONITORING OF BLOOD LACTATE AND TARGETING OF BLOOD LACTATE VIA NUTRITIONAL SUPPORT

APPLICATION PRIORITY DATA

The current patent application claims priority as a continuation of U.S. patent application Ser. No. 15/408,152 by Horning and Brooks, filed on Jan. 17, 2017 titled "CONTINUOUS MONITORING OF BLOOD LACTATE AND ONGOING TARGETING OF BLOOD LACTATE VIA NUTRITIONAL SUPPORT", which claims priority as a continuation of U.S. patent application Ser. No. 14/941,197 (U.S. Pat. No. 9,687,011) by Horning and Brooks, filed on Nov. 13, 2015 titled "BLOOD LACTATE RANGE TARGETS AND NUTRITIONAL FORMULATIONS AND PROTOCOLS TO SUPPORT PATIENTS", which claims priority as a continuation of U.S. patent application Ser. No. 14/043,703 (U.S. Pat. No. 9,232,815) by Horning and Brooks, filed on Oct. 1, 2013 titled "BLOOD LACTATE RANGE TARGETS AND NUTRITIONAL FORMULATIONS AND PROTOCOLS TO SUPPORT PATIENTS", which claims priority to U.S. provisional patent application 61/795,819 filed on Oct. 25, 2012 by Horning and Brooks. The current patent application also claims priority as continuation-in-part of U.S. patent application Ser. No. 13/903,929 filed on May 28, 2013 titled "SYSTEMS AND METHODS TO ESTIMATE NUTRITIONAL NEEDS OF HUMAN AND OTHER PATIENTS" which claims priority to U.S. provisional patent application 61/795,819 filed on Oct. 25, 2012 by Horning and Brooks. The current patent application claims priority as a continuation of U.S. patent application Ser. No. 15/728,880 by Horning and Brooks, filed on Oct. 10, 2017 titled "CONTINUOUS MONITORING OF BLOOD LACTATE AND ONGOING TARGETING OF BLOOD LACTATE VIA NUTRITIONAL SUPPORT", which claims priority as a continuation of U.S. patent application Ser. No. 15/408,152 by Horning and Brooks, filed on Jan. 17, 2017 titled "CONTINUOUS MONITORING OF BLOOD LACTATE AND ONGOING TARGETING OF BLOOD LACTATE VIA NUTRITIONAL SUPPORT", which claims priority as a continuation of U.S. patent application Ser. No. 14/941,197 (U.S. Pat. No. 9,687,011) by Horning and Brooks, filed on Nov. 13, 2015 titled "BLOOD LACTATE RANGE TARGETS AND NUTRITIONAL FORMULATIONS AND PROTOCOLS TO SUPPORT PATIENTS", which claims priority as a continuation of U.S. patent application Ser. No. 14/043,703 (U.S. Pat. No. 9,232,815) by Horning and Brooks, filed on Oct. 1, 2013 titled "BLOOD LACTATE RANGE TARGETS AND NUTRITIONAL FORMULATIONS AND PROTOCOLS TO SUPPORT PATIENTS", which claims priority to U.S. provisional patent application 61/795,819 filed on Oct. 25, 2012 by Horning and Brooks. All of the above-listed patents and patent applications are incorporated by reference in their entirety.

FIELD OF THE INVENTION

The present disclosure generally relates to the field of medical treatment. More specifically, the invention presents systems and methods to ascertain the metabolic state and nutritional needs of a patient, which can be thought of as the body energy state ("BES") of the patient. Assessment of the BES of the patient is critical information to treat and nourish (feed) the patient appropriately. Such assessment is based on ongoing and dynamic estimates of the biomarker fractional gluconeogenesis, which is the % of body glucose production that comes from gluconeogenesis. Methods, systems and materials for patient nutritional treatment and feeding based on estimation of this biomarker are also provided.

BACKGROUND OF THE INVENTION

Glucose is a basic fuel of the human body (as well as of many other organisms) and is delivered throughout the body through the blood. The rate of glucose production, also referred to as glucose rate of appearance and glucose Ra, is about 2-3 mg/min/kg of body weight in a healthy person while at rest, and can be as high as 8 mg/min/kg or more under stress such as exercise or illness. Pyruvate and lactate, which are both gluconeogenic precursors and products of glucose catabolism, are also basic fuels of the human body and other organisms.

Glucose, a six-carbon (hexose) sugar, is an essential fuel energy source for several vitally important organs and tissues in the body, including the brain and nerves that require a continuous glucose supply, including after injury. Not surprisingly, glucose is an important and tightly regulated metabolite.

Glucose Ra should not be confused with blood concentration of glucose, also called [glucose]. The latter is a simple measure of the total amount of glucose in the blood, as opposed to the rate of production. The [glucose] is a common measurement taken from a blood samples, as in standard doctor office visits and home diabetes diagnostics. This value can vary significantly in resting individuals, but generally averages about 90-100 mg/dl blood or 5.5 mM. Physiologically, glucose can appear in the blood of a person by three major means: delivery from ingested carbohydrate-containing foods, hepatic glycogenolysis ("GLY"), and gluconeogenesis ("GNG") (hepatic and renal). The recommended dietary allowance for carbohydrate-containing foods is about 130 g/day, a value determined to be the minimal daily brain glucose requirement (8) (note that non-patent literature citations are made as numbers in parentheses, and the corresponding references are listed at the end of this specification). Hence, dietary carbohydrate and total nutrient inadequacy will reflexively cause increased GLY and GNG to maintain glucose requirements for the brain, other tissues with high glucose needs (nerves, red blood cells, kidneys) and the body in general.

Glucose production occurs by GLY and GNG. It is generally better if the majority of glucose production is from GLY. This is because GLY is an efficient process of glucose production, in that it is simple breakdown of glycogen, a glucose polymer stored mainly in the muscles, liver and kidneys. Normally, at rest, in a nourished state, most glucose is produced by GLY (typically over 75%). This number can decrease under stress such as exercise or illness, as the body needs to produce more glucose than can be provided by GLY.

Gluconeogenesis ("GNG") describes essentially all pathways for producing glucose other than glycogenolysis ("GLY"). GNG produces glucose from carbon substrates such as pyruvate, lactate, glycerol, and gluconeogenic amino acids, among others. These can be termed GNG precursors. GNG is less efficient than GLY in terms of glucose produced per unit of stored energy because of the more complex pathways needed to produce it. Since it is less efficient than GLY, it is generally not preferred by the body, but can be used to produce glucose as needed. GNG is less efficient than GLY in other ways as well. The work of raising a GNG precursor to the level of glucose 6-phosphate and glucose requires significant energy input, and important body constituents such as lean body mass, muscle are often degraded to provide precursor materials for the process. GNG also may be used to access glycogen stored elsewhere in the body instead of direct conversion of that glycogen to glucose.

The current art in the measurement of metabolic state and treatment has at least two significant categories of problems. One is that no biomarker measurements, either alone or in combination, are used in the current art to give an accurate picture of the overall BES of a patient. To the degree that measurements are made in the current art, such as with [glucose], they are inadequate indicators of the BES.

The biomarker [glucose], is well known in the art and simple to assess from a blood test. While a large shift (either low or high) in [glucose] can be cause for concern and inform the type of feeding the patient receives, it does not provide a good indicator of the BES of a patient, especially within its typical ranges. Indeed, the maintenance of blood glucose homeostasis is a top physiological priority, and there are diverse and redundant body mechanisms to maintain blood [glucose]. Thus a normal [glucose] may belie metabolic stresses that are going on, with the body working very hard to maintain [glucose]. Among those mechanisms are GNG, a critically important process about which the blood [glucose] measurement provides no direct information.

Another biomarker, glucose rate of appearance ("Ra"), gives only a slightly better indicator of the BES of the patient. A high glucose Ra, for example, indicates that the patient may be experiencing a stress (such as injury, exercise or starvation) that has induced a high glucose production. While this is a somewhat useful, there is need for a biomarker that is a more precise indicator of BES. In addition, determination of glucose Ra is complex, time consuming and costly. It requires labeled glucose to be given to the patient, typically glucose with deuterium (typically noted as simply D or $^2H$ as opposed to merely H, hydrogen), or carbon 13 ($^{13}C$), and comparison of labeled and non-labeled glucose (the latter produced by the glucose pathways) to determine Ra (80).

The complex, costly and time-consuming process of determining glucose Ra with stable isotopes of H (typically deuterium) or $^{13}C$-glucose is well described in the literature (2, 26, 55). It is typically done as follows. Control subjects or patients receive a primed continuous infusion of $[6,6-^2H]$ glucose, i.e., $D_2$-glucose, glucose with two deuteriums on carbon number 6 (C-6) diluted in 0.9% sterile saline and tested for pyrogenicity and sterility prior to infusion. To hasten achievement of a constant blood isotopic enrichment, a priming bolus of perhaps about 125 times the continuous per minute infusion rate, or about 250 mg $D_2$-glucose, is infused over several min prior to commencement of a continuous tracer infusion of 2.0 mg·min$^{-1}$ $D_2$-glucose. In this manner, isotopic equilibration in the blood can be achieved in 60-90 min (about half the time to isotopic equilibration in blood if a priming tracer dose is not given).

To verify when isotopic equilibration has been achieved, several ml of blood is drawn serially. Verification can be done by mixing in several volumes of 6-8% perchloric acid ("PCA"), and the deproteinized supernatant analyzed by means of forming a penta-acetate derivative followed by analysis using gas chromatography/mass spectrometry ("GC/MS").

For simultaneous concentration analysis, known amounts of a labeled internal standard, such as uniformly labeled glucose, where each carbon of the glucose is labeled, by for example, the carbon 13 isotope, thus noted [U-$^{13}C$]glucose, is used. The glucose molecule thus has an increased mass of about 6 atomic units ("au") (m+6). This labeled glucose is added to the supernatant of control subject or patient samples collected in perchloric acid. To separate glucose, samples are neutralized with 2N KOH and transferred to cation resin, ion exchange columns such as 50W-X8 (from Bio-Rad Laboratories). Glucose is eluted first with doubly deionized $H_2O$ (the anions, and cations, by contrast, are retained on the column).

The glucose ion-exchange effluent is reduced by lyophilization and derivatized by resuspending the lyophilized sample in a small amount (e.g., 1 ml) of methanol, a small amount [e.g., 200 microliter (µl)] is transferred to a 2 ml microreaction vial and dried under $N_2$ gas. A small amount (e.g., 100 µl) of a 2:1 acetic anhydride-pyridine solution is added to each sample vial and heated at 60° C. for 10 min. Samples are again dried under $N_2$ gas, resuspended in a small amount (e.g., 200 µl) of ethyl acetate, and transferred to micro vials for analysis.

Glucose isotopic enrichment ("IE") is determined by GC/MS, for instance with a GC model 6890 series and MS model 5973N, from Agilent Technologies) of the penta-acetate derivative, where methane is used for selected ion monitoring of mass-to-charge ratios (m/z) 331 (non-labeled glucose), 332 (M+1 isotopomer, [1-$^{13}C$]glucose), 333 (M+2 isotopomer, $D_2$-glucose), and 337 (M+6 isotopomer, [U-$^{13}C$]glucose, the internal standard). Whole blood glucose concentration is determined by abundance ratios of 331/337, Selected ion abundances are compared against external standard curves for calculation of concentration and isotopic enrichment.

Therefore there is a need in the art for a biomarker that is a good indicator, by itself, of BES, as well as simple and effective methods of estimating that biomarker.

SUMMARY OF THE INVENTION

The invention presents systems and methods to ascertain the metabolic state and nutritional needs of a patient. Such assessment is based on ongoing and dynamic estimates of the biomarker fractional gluconeogenesis, which is the % of body glucose production that comes from gluconeogenesis. Methods, systems and materials for patient nutritional treatment and feeding based on estimation of this biomarker are also provided. The invention includes, but is not limited to the following, with some variation.

According to an embodiment of the present disclosure, the invention provides a method for estimating the fractional gluconeogenesis of a patient, administering a label to the patient, taking a blood sample from the patient, analyzing glucose or a glucose derivative from the blood sample, obtaining a value for fractional gluconeogenesis based on abundance from one or more mass spectra, obtaining a value for fractional gluconeogenesis plus glycogenolysis from one or more mass spectra, and estimating fractional gluconeogenesis.

According to an embodiment of the present disclosure, the invention provides a method for providing nutritional support to a patient, including administering a label to the patient, taking a blood sample from the patient, analyzing glucose or a glucose derivative from the blood sample, obtaining a value for fractional gluconeogenesis based on abundance from one or more mass spectra, obtaining a value for fractional gluconeogenesis plus glycogenolysis from one or more mass spectra, using the value to create to estimate fractional gluconeogenesis, and administering a parenteral nutritive formulation to the patient based upon the fractional gluconeogenesis estimate. The label may be deuterium.

According to an embodiment of the present disclosure, the invention provides a method for estimating the fractional gluconeogenesis of a patient, the method including, administering a label to the patient, estimating the fraction of body water that has been labeled, using this estimate to create a baseline for the amount of total glucose production, estimating an amount of glucose production only from gluconeogenesis by measuring the label, and estimating the patient's fractional gluconeogenesis.

The methods can include a water labeled with deuterium, wherein less than about 1% of the body water is labeled, wherein the body water is labeled with an initial bolus, wherein the body water is continually labeled by ongoing infusion of labeled water, wherein the glucose derivative is a penta-acetate glucose molecule with molecular weight of about 390, wherein part of the estimation is based on the abundance of the label on one or more of glucose carbons 1, 3, 4, 5, 6, wherein part of the estimation is based on the abundance of the label on glucose carbon 2, wherein glucose Ra is estimated to further provide an estimate of absolute rate of GNG, and using a correction factor to correct for the fraction of the molecule that exists in a state that includes the label. The method provides for molecule analysis in a gas chromatograph mass spectrometer. The method provides, upon estimating the fractional gluconeogenesis, the patient is administered a parenteral nutritive formulation, wherein the formulation may contain MCC or GNG precursor or both, pyruvate or lactate or both, wherein the formulation is administered or increased if the estimated fractional GNG is above about 25% or 35%, wherein the formulation is stopped or decreased if the estimated fractional GNG is below about 15% or 20%.

According to an embodiment of the present disclosure, the invention provides a parenteral nutritive formulation for feeding a patient to decrease or stabilize fractional gluconeogenesis, including water and MCC or GNG precursor or both. It also provides a parenteral nutritive formulation for feeding a patient with injury or illness, including water and MCC or GNG precursor or both. It also provides parenteral nutritive formulation for feeding a patient to decrease or stabilize fractional gluconeogenesis, the formulation including water and lactate or pyruvate or both, and one or more salts, wherein the formulation has an osmolality less than about 310 mOsm.

The formulations may also include one or more salts, one or more of $Na^+$, $K^+$, $Ca^{++}$, $Mg^{++}$, and $H_2PO_4^-$, a label such as deuterium, have an osmolality of less than about 310 mOsm, where one of the MCCs or GNGs is lactate or pyruvate or both, where one of the MCCs or GNGs is an amino acid where one of the MCCs or GNGs is a GNG precursor that naturally occurs in the body, where one of the MCCs or GNGs is a compound that does not naturally occur in the body but that can be used as a GNG precursor, where one of the MCCs or GNGs is glycerol or glycerol tri-lactate. The formulation may be administered at a rate of about 3 mg/kg/min, where kg is kg of patient body weight and 3 mg is the amount of MCC or GNG in the formulation, may be administered at a rate of about 50 micro moles per kg of body weight per minute (µMoles/kg/min), where kg is kg of patient body weight and 50 µM is the amount of MCC or GNG in the formulation, administered or increased if estimated fractional GNG is above about 25% or 35%, or decreased or stopped if estimate of fractional gluconeogenesis is below about 20% or 15%.

The formulations may include a label such as deuterium and one or more salts. They may contain or more of the following: Na+, $K^+$, $Ca^{++}$, $Mg^{++}$, and $H_2PO_4^-$. They may have $Na^+$, $K^+$, $Ca^{++}$, $Mg^{++}$, and $H_2PO_4^-$ provided in the ratio of about 145, 4, 2.5, 1.5, and 1.0 respectively. They may have MCC or GNG precursor or both. The formulation may have an osmolality of less than about 310 mOsm. The formulation may have an MCCs or GNGs that is lactate or pyruvate or both, an amino acid, a GNG precursor that naturally occurs in the body, a compound that does not naturally occur in the body but that can be used as a GNG precursor, glycerol tri-lactate or arginyl lactate. The formulation may be administered at a rate of about 3 mg/kg/min, where kg is kg of patient body weight and 3 mg is the amount of MCC or GNG precursor in the formulation and may be administered or increased if estimated fractional GNG is above about 25% or 35%, or decreased or stopped if estimate of fractional gluconeogenesis is below about 20% or 15%. The formulations may be parenteral, used to estimate fractional GNG, used to stabilize or decrease fractional GNG. The label may be incorporated into glucose. The label may be differentially incorporated into glucose depending on whether it is incorporated via the gluconeogenesis pathway or via the glycogenolysis pathway.

The nutritive formulations may include deuterium, lactate or pyruvate or both, and one or more salts, may have an osmolality of less than about 310 mOsm, may have one more of the following: Na+, $K^+$, $Ca^{++}$, $Mg^{++}$, and $H_2PO_4^-$, may be parenteral. The nutritive formulation may be used to decrease or stabilize fractional gluconeogenesis, and include deuterium, lactate or pyruvate or both, and one or more salts, may have an osmolality of less than about 310 mOsm, and may have one more of the following: $Na^+$, $K^+$, $Ca^{++}$, $Mg^{++}$, and $H_2PO_4^-$.

In all of the systems and methods, various labels may be used, including deuterium, such as in deuterium oxide (water), and sometimes at a concentration of less than about 1% of the water. The formulations may be enteral or parenteral.

According to an embodiment of the present disclosure, the invention provides a method for estimating the fractional gluconeogenesis of a patient, the method including, from a patient blood sample, analyzing the glucose or one or more derivatives of the glucose, or both, the blood sample comprising glucose and a label, obtaining a value or set of values for gluconeogenesis, obtaining a value or set of values for total glucose production, and the above to estimate fractional gluconeogenesis.

According to an embodiment of the present disclosure, the invention provides a method for estimating the fractional gluconeogenesis of a patient, including, from a patient blood sample, analyzing the glucose or one or more derivatives of the glucose, or both, the blood sample comprising glucose and a label, estimating the fraction of body water that has been labeled, using this to create a baseline for the amount of total glucose production; estimating an amount of glucose production from gluconeogenesis by measuring the label and using above to estimate the fractional gluconeogenesis.

According to an embodiment of the present disclosure, the invention provides a method for aiding in the estimation of the fractional gluconeogenesis of a patient, the method including, from a patient blood sample, analyzing the glucose or one or more derivatives of the glucose, or both, the blood sample comprising glucose and a label, obtaining a value or set of values for gluconeogenesis based on the abundance of the label on one or more of glucose carbons 1, 3, 4, 5, 6, and obtaining a value or set of values for total glucose production based on the abundance of the label on glucose carbon 2, The method further includes transmitting these values or sets of values and using them to calculate a value or set of values for estimated fractional gluconeogenesis.

According to an embodiment of the present disclosure, the invention provides a method for aiding in the estimation of the fractional gluconeogenesis of a patient, the method including from a patient blood sample, analyzing the glucose or one or more derivatives of the glucose, or both, the blood sample comprising glucose and a label, estimating the fraction of body water that has been labeled, using this estimating to obtain a value or set of values as a baseline for the amount of total glucose production and obtaining a value or set of values for gluconeogenesis by measuring the label. The method also includes transmitting the value or set of values obtained and using them to calculate a value or set of values for estimated fractional gluconeogenesis.

According to an embodiment of the present disclosure, the invention provides a method for estimating the fractional gluconeogenesis of a patient, the method including receiving a value or set of values for gluconeogenesis, receiving a value or set of values for total glucose production, using (a) and (b) to estimate fractional gluconeogenesis.

According to an embodiment of the present disclosure, the invention provides a method for estimating the fractional gluconeogenesis of a patient, the method including receiving a value or set of values for gluconeogenesis, receiving a value or set of values for fraction of body water that has been labeled and using the above to estimate fractional gluconeogenesis.

According to an embodiment of the present disclosure, the invention provides a method of providing nutrition to a patient, the method including obtaining a value or set of values for estimated fractional gluconeogenesis, and decreasing, increasing or maintaining nutritional support based on the value or set of values for estimated fractional gluconeogenesis. Nutritional support may be stopped or decrease if the value or set of values for estimated fractional gluconeogenesis is above about 25%. Nutritional support is begun or increased if the value or set of values for estimated fractional gluconeogenesis is below about 15%.

According to an embodiment of the present disclosure, the invention provides a method of providing nutritional support to a patient, the method including, (a) administering a label, (b) administering a formulation, (c) taking one or more blood samples from the patient, and (d) measuring incorporation of the label into glucose in order to estimate fractional gluconeogenesis. In the method (c) and (d) may be done on a periodic basis in order to provide an ongoing estimate of fractional gluconeogenesis.

According to an embodiment of the present disclosure, the invention provides a method for estimating the fractional gluconeogenesis of a patient, the method including, (1) administering a label, (b) administering a formulation, (c) taking one or more blood samples from the patient, (d) analyzing glucose or a glucose derivative from the blood sample, (e) obtaining a value for fractional gluconeogenesis, (f) obtaining a value for fractional gluconeogenesis plus glycogenolysis, and (g) using (e) and (f) to estimate fractional gluconeogenesis. In the method (c)-(g) are done on a periodic basis in order to provide an ongoing estimate of fractional gluconeogenesis.

According to an embodiment of the present disclosure, the invention provides a method for estimating the fractional gluconeogenesis of a patient, the method including, (a) administering a label, (b) administering a formulation, (c) taking one or more blood samples from the patient, (d) estimating the fraction of body water that has been labeled, (e) using the estimating in (d) to create a baseline for the amount of total glucose production, (f) estimating an amount of glucose production only from gluconeogenesis by measuring the label, and (g) using (e) and (f) to estimate the patient's fractional gluconeogenesis. In the method (c)-(g) are done on a periodic basis in order to provide an ongoing estimate of fractional gluconeogenesis.

According to an embodiment of the present disclosure, the invention provides a method of modulating the fractional gluconeogenesis of a patient, the method including: (a) administering a label, (b) administering a formulation, (c) taking one or more blood samples from the patient, (d) measuring incorporation of the label into glucose in order to estimate fractional gluconeogenesis, and (e) modifying the composition and rate of infusion or both of the formulation to target a fractional gluconeogenesis range. In the method (c) and (d) are done on a periodic basis in order to provide an ongoing estimate of fractional gluconeogenesis. The gluconeogenesis range targeted may be about 15-35% or about 20-25%.

According to an embodiment of the present disclosure, the invention provides a method of providing nutritional support to a patient, the method including, (a) estimating the blood lactate concentration of the patient, (b) providing, increasing, decreasing or ceasing a formulation to the patient based on the blood lactate concentration.

According to an embodiment of the present disclosure, the invention provides a method of targeting a blood lactate concentration in a patient, the method including, (a) estimating the blood lactate concentration of the patient, and (b) increasing, decreasing or maintaining or ceasing a formulation to achieve the target blood lactate concentration.

According to an embodiment of the present disclosure, the invention provides a method of affecting the fractional gluconeogenesis of a patient, the method including: (a) estimating the blood lactate concentration of the patient, (b) increasing, decreasing or maintaining a first formulation to achieve a target blood lactate concentration, (c) estimating the fractional gluconeogenesis of the patient, and (d) providing a second formulation to the patient in order to achieve a target fractional gluconeogenesis range.

According to an embodiment of the present disclosure, the invention provides a formulation including: (a) GNG precursor or MCC or both, and (b) one or more salts, the formulation capable of affecting blood lactate concentration.

According to an embodiment of the present disclosure, the invention provides a formulation including: (a) GNG precursor or MCC or both, the formulation capable of reducing or stabilizing catabolism or cachexia or both. The formulations of the invention throughout are capable of affecting blood lactate concentration, capable of reducing or stabilizing catabolism and cachexia. The formulations may include glucose polymer.

According to an embodiment of the present disclosure, the invention provides method of providing nutritional support to a patient, the method including: (a) providing a formulation comprising a GNG precursor or MCC or both, wherein the formulation is capable of affecting the blood lactate concentration of the patient, and may target a blood lactate concentration is above about 1-8 mM.

According to an embodiment of the present disclosure, the invention provides a formulation for providing nutritional support for physical activity, the formulation including: GNG precursor or MCC or both, and one or more salts.

According to an embodiment of the present disclosure, the invention provides method of providing nutritional support for physical activity, the method including providing a formulation comprising a GNG precursor or MCC or both and one or more salts, and may target a blood lactate concentration is above about 1-8 mM.

The method and formulations of the invention may label the body water with an initial bolus or ongoing infusion or both. The value or set of values for total glucose production can also represent % body water labeled, and can be based on the abundance of the label on one or more of glucose carbons 1, 3, 4, 5, 6, The value or set of values for gluconeogenesis can be based on the abundance of the label on glucose carbon 2, The glucose derivative analyzed is a penta-acetate glucose molecule with molecular weight of about 390, or has a molecular weight of about 169, or 172. The value or set of may include a correction factor. Glucose Ra may be estimated to further provide an estimate of absolute rate of gluconeogenesis. The formulation of the method may include GNG precursor or MCC or both, pyruvate or lactate or both, a GNG precursor or MCC other than lactate. The formulation may be administered or increased if the estimated fractional gluconeogenesis is above about 25%. The formulation may be stopped or decreased if the estimated fractional gluconeogenesis is below about 20%.

The methods and formulations may have $Na+$, $K^+$, $Ca^{++}$, $Mg^{++}$, and $H_2PO_4$ $Na^+$, $K^+$, $Ca^{++}$, $Mg^{++}$, and $H_2PO_4^-$ in the ratio of about 145, 4, 2.5, 1.5, and 1.0 respectively, and a label such as deuterium. The osmolality may be less than about 310 mOsm.

The formulations may be administered at a rate of about 3 mg/kg/min, where kg is kg of patient body weight and 3 mg is the amount of GNG precursor or MCC in the formulation or at a rate of about 50 mMoles/kg/min, where kg is kg of patient body weight and 50 mM is the amount of GNG precursor or MCC in the formulation. The formulations may have zero or close to zero nutritional content to accommodate a patient that is adequately fed. An initial bolus of label may be given to the patient and the initial bolus labels less than about 1% of the patient's body water and the label may be deuterium. The label may be in a nutritional formulation. The methods and formulations may be used with a patient that is a healthy individual engaged physical activity. They may target a fractional gluconeogenesis range and affect fractional gluconeogenesis.

BRIEF DESCRIPTION OF THE DRAWINGS

The described techniques and mechanisms, together with other features, embodiments, and advantages of the present disclosure, may best be understood by reference to the following description taken in conjunction with the accompanying drawings, which illustrate various embodiments of the present techniques and mechanisms. In the drawings, structural elements having the same or similar functions are denoted by like reference numerals.

DETAILED DESCRIPTION OF THE INVENTION

Gluconeogenesis ("GNG")

Figure 1:
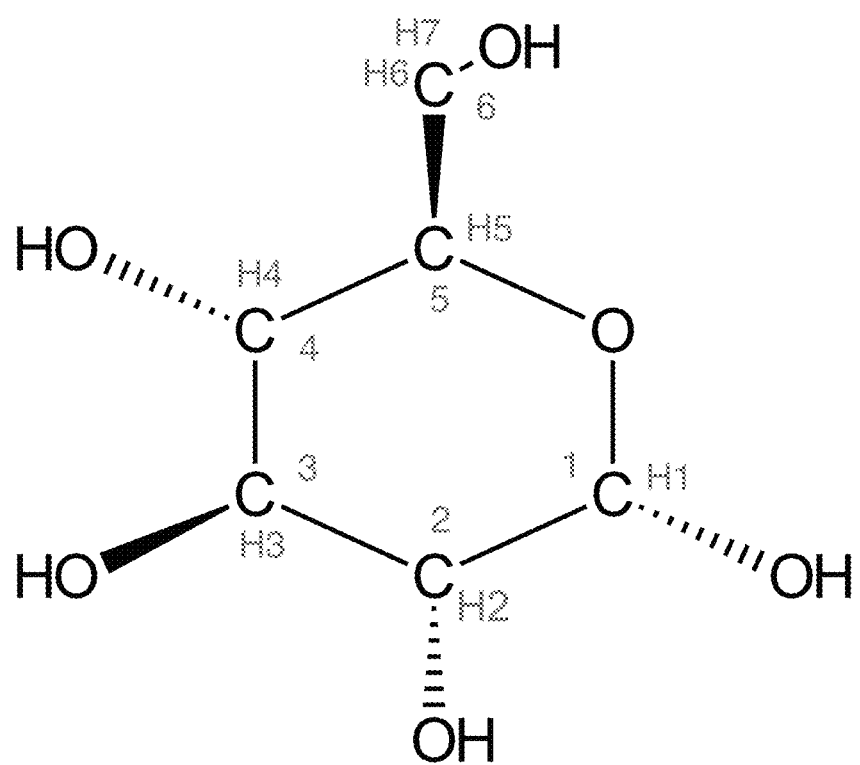
FIG. 1 is a standard chemical representation/illustration of the molecule glucose, approximate molecular weight ("MW") 180, in the biologically dominant alpha-D-glucose confirmation.

That superior biomarker for assessing the BES of a patient, as disclosed in the present invention, is fractional GNG, that is, the % of total glucose production that comes from GNG.

Various embodiments of the present disclosure provide systems and mechanisms for estimating fractional GNG in a patient. The disclosed invention includes systems and methods for determining the nutrition state and needs of the patient also based on the absolute rate of GNG and the rate of glucose appearance, among other measures. It also includes systems and methods for treating patients using nutritive formulations as disclosed. In a preferred embodiment of the invention, we estimate fractional GNG in a patient, and use this to prescribe the rates of parenteral and enteral energy substrate administration to support patient recovery. Some of the expected benefits of this treatment are an increased healing rate and decreased hospitalization time. Importantly, in some patients the results of our invention may make the difference between poor versus good recovery, and in other patients, the difference between life and death. The course of discovery to use fractional GNG as a biomarker of BES and needs for energy substrate nutrition is described here.

Inspiration for the invention arose in part from the inventors' cumulative professional experiences in public service, education, and consultation in industry and metabolic research in exercise physiology. In particular, metabolic stresses such as the oxygen-limited condition of high altitude, cigarette smoking, and the personal experience of one inventor, Michael Horning ("MAH") observing the metabolic effects of a traumatic brain injury ("TBI") to a family member served to help the inventors conceive and reduce the invention to practice.

Note that in the current art, the term glycemia is loosely used to mean the state of the body and blood glucose, in particular [glucose]. But the current invention takes the term and makes it much more precise, by describing underlying mechanisms of glycemic control such as GNG and fractional GNG. The term "tight" glycemic control is sometimes used loosely in the current art to mean a more nuanced approach to control of glucose, but is also not very precise. The current invention provides systems and methods for a sort of "exquisite" glycemic control that is vastly superior at estimating the patient's BES and meeting the patient's nutritional needs.

In 2006, Ruthe Horning ("RH"), mother of MAH, was struck by a car while riding her bicycle in Pacific Grove, Calif. She suffered a severe traumatic brain injury, and was rushed into emergency surgery for her first craniectomy. Later that night she received a second emergency craniectomy (a bilateral craniectomy) to help reduce the swelling created by the subdural hematoma resulting from the injury to her brain, and her chances of survival (or good recovery) were uncertain. Over the next several weeks of visiting RH in the intensive care unit ("ICU") MAH made many observations concerning the metabolic status of his mother including increased heart rate and temperature while she was in a coma.

From experience and training in science, MAH believed by gross observation of RH's condition and vital signs, that his mother's metabolic state was not that of a resting person, but rather her metabolism was more like that of an exercising person. Coupled with those observations MAH also noted that RH's recovery accelerated when she was eventually given enteral nutrition, at his urging. This nutritional source resulted in a marked improvement and she gained strength and mental faculties almost immediately.

RH was in serious need of nutritional support, but was underfed as the result of state of the art treatment. Many months later RH regained enough mental faculties to start to comprehend the enormity of the accident and her injuries, and MAH made a commitment to her that he would find a better treatment for injured patients. Thus a compelling need was articulated that led to a path of discovery of the current invention. The need, in part, was for one or more key biomarkers of BES, methods for measuring these biomarkers, and nutritional treatment methods and formulations based on such measurements.

Over the years, the two inventors began exploring for the particular biomarkers that could be used for BES assessment and treatment. The inventors were looking for an ideal diagnostic method to use in evaluating metabolic state and nutritional needs, or BES, of an ill or injured hospitalized human or animal patient. Over time, based on many studies and empirical observation, it became clear to the inventors that fractional GNG, that is % of glucose production from GNG, was the key biomarker with regard to BES. While glucose Ra is somewhat useful (and using glucose Ra and fractional GNG, one can also determine GNG rate of production, since fractional GNG×glucose Ra=GNG rate of production), fractional GNG alone can be used to accurately assess the BES and nutritional needs of a patient.

While there are methods in the art that can be used to estimate fractional GNG and thus assess BES (3, 55-57) the current invention discloses new, improved, simplified means to estimate fractional GNG.

The current art views a sedentary or unconscious patient as resting, and thus not needing any nutritional support beyond that of a resting patient, because he or she is physically inactive. The current art also may view some critical illnesses as hypermetabolic, and in need of additional caloric support. Even in such cases, an accurate assessment of BES does not exist, and the nutritional support is often delayed and the nutritional management is based on formulas not necessarily specific to the patient's needs. Over time, the inventors realized that many patients, including comatose, ill or injured persons, are often in a catabolic (body tissue and energy storage breakdown) state because of the stresses of illness or injury. Based on various empirical observations, the inventors have seen such ill or injured patients with fractional GNGs well above 25%, which is similar to that of stressed, intensely exercising individuals or even starving ones.

In fact, by definition, GNG involves catabolism of body tissues to support production of glucose, since it is a less favored, inefficient method of glucose production. Glucose is an essential body nutrient and unique fuel for tissues such as brain, nerves, kidneys and red blood cells. To heal and gain strength an ill or injured person needs macronutrient nutrition, in particular, including glucose or glucose precursors.

Another embodiment uses an estimate of the absolute rate of GNG in mg/kg/min, in addition to the % GNG, as a biomarker. This requires an estimate of glucose Ra, in addition to fractional GNG, in order to yield and estimate of the absolute rate of GNG (absolute rate GNG=glucose Ra×fractional GNG).

In the late 1970's and early 1980s, using radioactive tracers of glucose and lactate the inventors, among others (11, 23) saw that exercise and exercise training increased the ability of laboratory rats to maintain normal blood glucose concentration (also referred to as [glucose]) by increased capacity for making new glucose via GNG, using precursors such as lactate. In humans and other mammals, lactate production takes place in working muscles, among other tissues, whereas the conversion of lactate to glucose generally takes place mostly in the liver and kidneys. With the advent of stable, non-radioactive isotopes, the inventors, among others, studied men resting and exercising in a laboratory at sea level and developed technology to measure gluconeogenesis in resting and exercising men. Then, in the late 1980s, the inventors, among others, were able to use stable isotopes to measure and compare glucose and lactate fluxes in men resting and exercising in a laboratory at sea level and then under the added stress of the 14,000 feet elevation on Pike's Peak (9, 10). Among the many remarkable findings of such studies were enhanced ability of the subjects to both produce and use lactate for energy, in part by converting lactate to glucose via GNG and directly oxidizing the remaining lactate.

In addition, using stable isotopes of glucose and lactate, the inventors, among others, (21, 22, 39) made measurements showing enhanced GNG from lactate in smokers compared to non-smokers while exercising. Subsequently, over the course of decades of experimentation the inventors became experts in the science and technology of studying human physiology and of using isotope tracers to measure various metabolite flux rates in humans and other mammals engaged in exercise and other above-mentioned stresses.

For the inventors, lessons learned in the laboratory were complimented by a far wider set of experiences that involved the acquisition and transfer of knowledge that occurred within the context of general research in the field. Areas of experience included providing consulting and other services to business, scientific and governmental organizations. Additional areas of experience included serving on review boards and providing editorial duties for scientific journals.

The invention benefits treatment of an ill or injured person by using fractional GNG as the critical biomarker. While the general concept of estimation of fractional GNG by itself is not new, see, for example (3, 14, 20, 26, 27, 73, 74) the invention introduces new and improved systems and methods for such estimation. The invention also further uses these estimates as a highly useful determinant of the balance of BES, e.g., catabolism vs. anabolism and nutritional needs of an ill or injured patient in order to treat, feed and provide nutrition to the patient appropriately. For discussion of the general concept of the general use of biomarkers and measurement of various other aspects of metabolic flux see, for example (28, 65).

In addition to other improvements, the invention includes the improvement of continually or dynamically estimating fractional GNG, thus providing an ongoing basis by which to understand the BES of the patient and thus treat the patient, in addition to point measurement of fractional GNG. The invention includes a new metabolic diagnostic test to assess fractional GNG to determine the underlying metabolic and nutritional status, or BES, of a patient. The scientific literature increasingly suggests that such measurements should be made, neither specifies how to specifically interpret such information in the context of the metabolic and nutritive state of the patient, nor how to proceed on this information in terms of formulations and amounts of such formulations (75). In underfed patients, the liver, and to a lesser extent the kidneys, are the body organs that make new glucose from GNG. The invention also includes using the information derived from the test above to articulate information on the metabolic state and nutritive needs of a patient.

Estimating Fractional GNG

In a preferred embodiment, fractional GNG is estimated, which alone can be used as a highly useful, even determinative biomarker of BES. The basic principle is to label a portion of the patient's body water and then to estimate the portion of glucose production that becomes labeled via the GNG pathway. Because a label such as deuterium can be incorporated onto different positional carbons of glucose depending on whether the glucose was produced by GLY or GNG, such labeling can be used to estimate fractional GNG in the invention.

To function as an effective precursor label, the proportion of body water to be labeled must be large enough to give an accurate measurement of isotopic enrichment in both body water and blood glucose by whatever detection mechanism is used to determine the isotopic enrichments. It should also be highly sensitive so that relatively small blood samples can be taken for comfort and efficacy, and to reduce the cost of isotopic labeling and analyses. In a preferred embodiment, that label is deuterium, that is, the hydrogens in the water are the deuterium isotope (written as $^2H$ or D) and $D_2O$ is added to body water.

This deuterated water (generally commercially available at >98% purity) is generally introduced intravenously to the patient. In a preferred embodiment, an amount of deuterated water that approximates 0.3-0.5% of body water is given to the patient as a bolus. This amount is typically estimated by assuming 70% of body weight is water. Within a few hours, the labeled water both equilibrates with body water and is incorporated into blood glucose via the GLY and GNG pathways due to rapid isomerization between fructose-6-phosphate and glucose-6-phosphate during the process of glucose production. The hydrogen atoms on carbon 2 on glucose will be labeled via glucose production in proportion to the labeling of body water, and can be used to validate the % labeling of body water number enriched with deuterium.

By contrast, hydrogen atoms on carbons 1, 3, 4, 5, and 6 of glucose will be enriched with deuterium during transit of precursors through the GNG pathway. The hydrogen atoms on carbons 1, 3, 4, 5, and 6 of glucose will be labeled equally during GNG due to isomerization of glyceraldehyde-3-phosphate to dihydroxyacetone phosphate by triose phosphate isomerase and a series of equilibration reactions between phosphoenolpyruvate and dihydroxyacetone phosphate. The abundance of label at each of these carbons thus each represent GNG enrichment, though the average of these carbons (or an average of some) can be used for a potentially more accurate measurement. Thus, for example, the fraction of hydrogen atoms enriched by deuterium on C-1 of glucose will be equal to that on C-5, but each will have an amount smaller than the enrichment at C-2 due to the combined pathways of GNG and GLY.

In a preferred embodiment, a blood sample is taken after this initial bolus, and the glucose is extracted using standard methods known in the art via solvents. In a preferred embodiment, the glucose is converted to the penta-acetate molecule shown in FIG. 2, approximate MW 390, so that this glucose derivative can be detected in a gas chromatograph ("GC") mass spectrometer ("MS"). The hydrogen-deuterium atoms on C-2 are removed during ionization so that we can isolate the carbons enriched by deuterium during GNG, thus obtaining the average GNG enrichment. This mass to charge (m/z) ion has a non-labeled molecular mass ("m") of 169 and charge ("z") of 1. If the ion is enriched with a deuterium at one of the carbons, then its m/z will be 170.

In one embodiment, the invention can be practiced without chromatography. Sugar measured without a chromatography step to isolate glucose from other blood sugars such as fructose and galactose would still be about 95% glucose, and so a meaningful number for glucose can be obtain without separation. Carbohydrate digestion produces a high percentage of glucose as the fundamental energy source for cell metabolism. Two other forms of sugars, galactose, and fructose, are also products of carbohydrate digestion. Despite the relatively high percentage of digested fructose and galactose (about 20%), after gastrointestinal absorption, the liver enzymes convert most of these sugars to glucose, resulting in the 95% number.

Of course, some of the ions will be enriched at more than one carbon, and by more than one isotope. For instance, endogenous (background) isotopic enrichment of carbon in body substances by ($^{13}C$) approximates 1.09%. Similarly, the endogenous (background) deuterium enrichment is very small, approximately 0.015%, and the target $D_2O$ enrichment in body water is approximately 0.3 to 0.5%, the background deuterium will not meaningfully affect estimation of fractional GNG as described here. It can in any case be corrected for, if desired.

The literature contains no reference for the method of determining fractional GNG and isotopic enrichment in body water following administration of $D_2O$ that we describe here. However, others have used different methods using measurements of the isotopic enrichment of glucose following administration of $D_2O$ and comparing to the enrichment in body water (20, 30, 45).

The ratio of 170/169 ions (further divided by 6, the number of hydrogen atoms on this ionized glucose fragment) divided by body water enrichment will thus yield an abundance value for fractional GNG. The body water enrichment value can either be taken from the bolus to body weight approximation described above (and, in a preferred embodiment, intended to be 0.3 to 0.5%), or estimated from the glucose carbon 2 enrichment via GLY as described in this equation:

Fractional GNG=((abundance 170/abundance 169)/6)/fraction of body water labeled

For reference, a standard chemical representation of glucose, approximate molecular weight ("MW") 180, in shown in FIG. 1 (specifically the biologically dominant confirmation alpha-D-glucose). That same glucose molecule with each of the 7 hydrogens replaced with the marker deuterium (D) is shown in FIG. 2.

Figure 2:
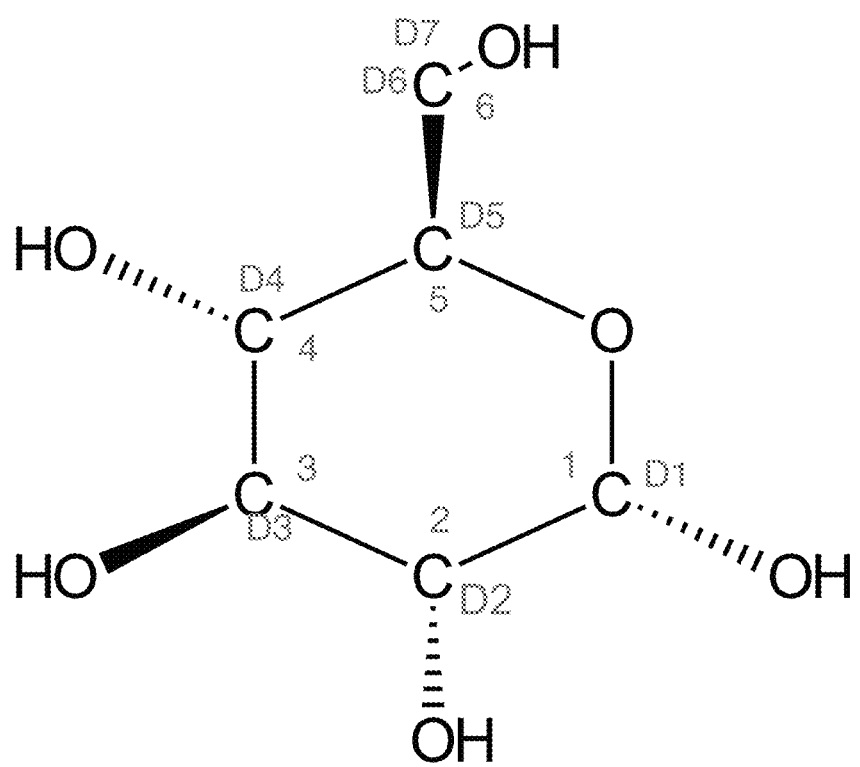
FIG. 2 is a standard chemical representation/illustration of the molecule glucose, with all seven hydrogens replaced with deuteriums (as labels).

FIG. 2 is a standard chemical representation/illustration of the molecule glucose, with all seven hydrogens replaced with deuteriums (as labels).

Figure 3:
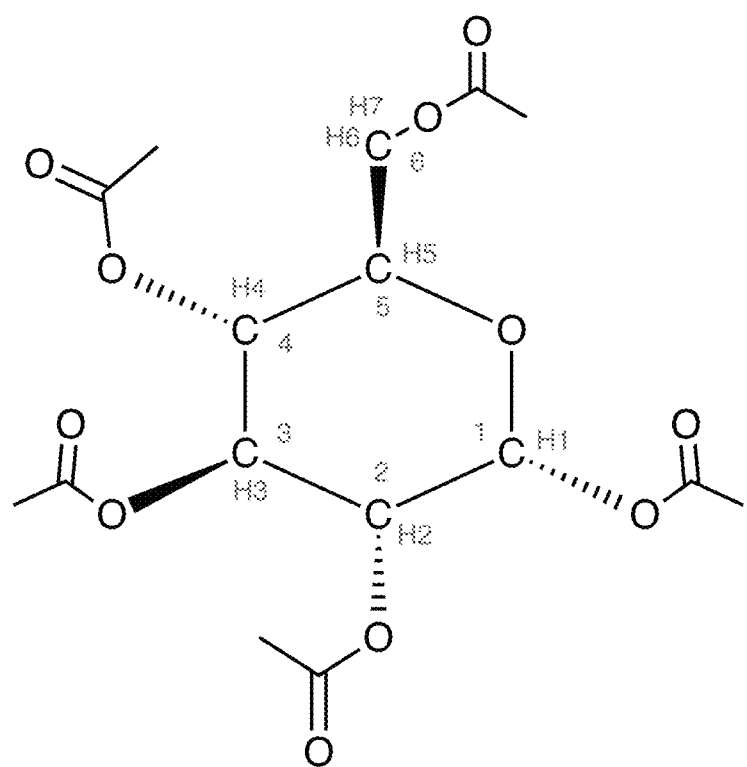
FIG. 3 shows the penta-acetate glucose derivative, approximate MW 390, that is part of the mass spectra analysis method, in a preferred embodiment of the invention.

FIG. 3 shows the penta-acetate glucose derivative, approximate MW 390, that is used in the GC/MS analysis method, in a preferred embodiment of the invention.

Figure 4:
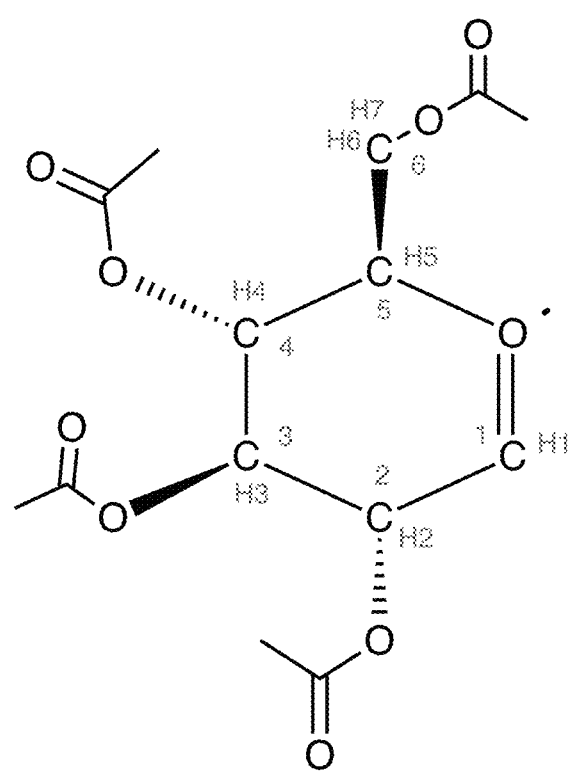
FIG. 4 shows a fragment of the penta-acetate glucose derivative with all of the hydrogens of interest still on the molecule, approximate MW 331, as well as the same molecule with different isotopes (MW 332, etc.)

FIG. 4 shows a fragment of the penta-acetate glucose derivative, approximate MW 331, as well as the same molecule with different isotopes (MW 332, etc.)

Figure 5:
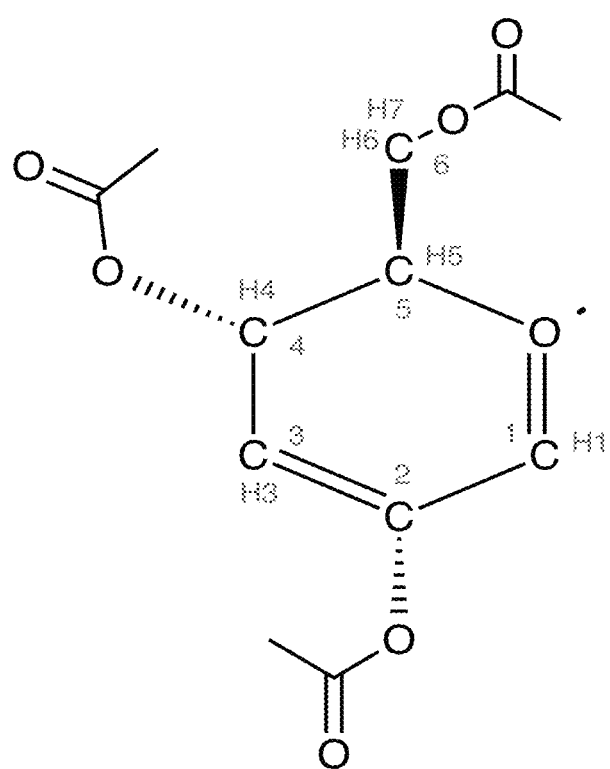
FIG. 5 shows a fragment of the penta-acetate glucose derivative, approximate MW 271, as well as the same molecule with different isotopes (MW 272, etc.)

FIG. 5 shows a fragment of the penta-acetate glucose derivative, approximate MW 271, as well as the same molecule with different isotopes (MW 272, etc.)

Figure 6:
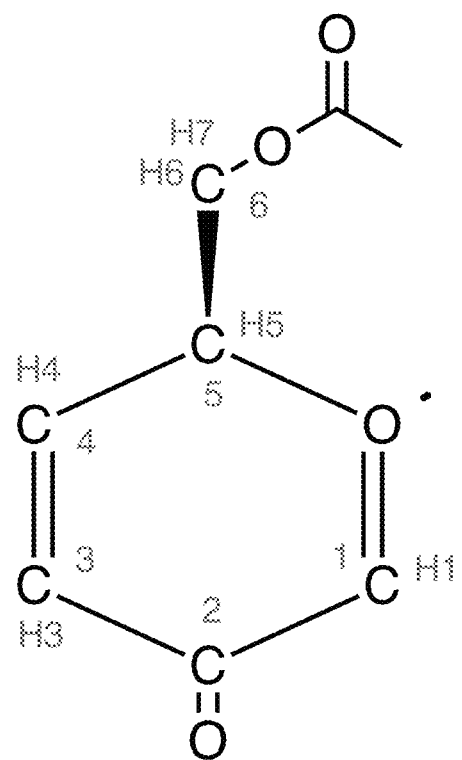
FIG. 6 shows another fragment of the penta-acetate glucose derivative, approximate MW 169, as well as the same molecule with different isotopes (MW 170, etc.)

FIG. 6 shows another fragment of the penta-acetate glucose derivative, approximate MW 169, as well as the same molecule with different isotopes (MW 170, etc.)

In a preferred embodiment of the invention the body water enrichment is taken from observing the abundance of the labeled penta-acetate glucose derivative MW 331. This ion has a non-labeled molecular weight of 331 and charge of 1, Since this ion retains all carbons and hydrogens of the base glucose molecule, it is enriched by both GLY and GNG, at one of the seven hydrogens associated with the six carbons of the glucose, resulting in an ion with molecular weight of 332, Thus the abundance of this molecule represents enrichment by both pathways. Enrichment at carbon 2 is by both pathways, and enrichment at the other carbons is only by GNG.

Figure 7:
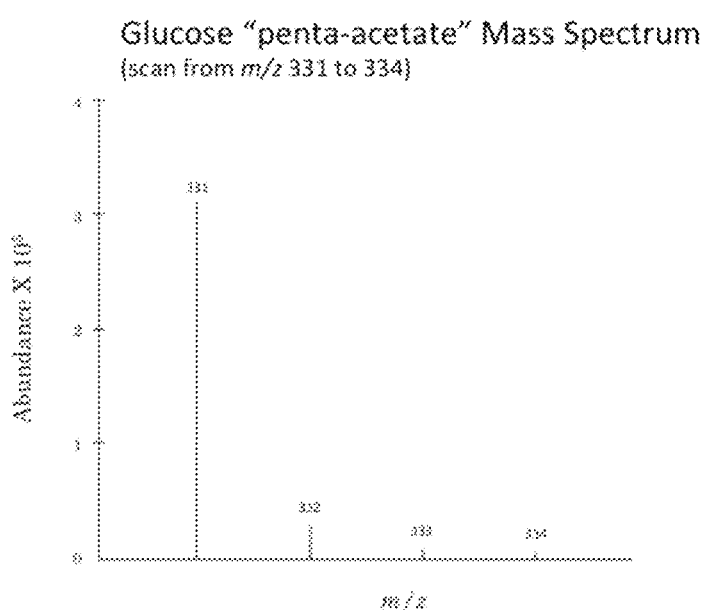
FIG. 7 shows a schematic mass spectrum focusing on the MW 331 and related ions.

FIG. 7 shows a schematic mass spectrum focusing on the 331 ion. As stated, relative abundance of the 332 ion (marked with one deuterium) vs. the 331 ion represents enrichment by both GLY and GNG pathways.

Figure 8:
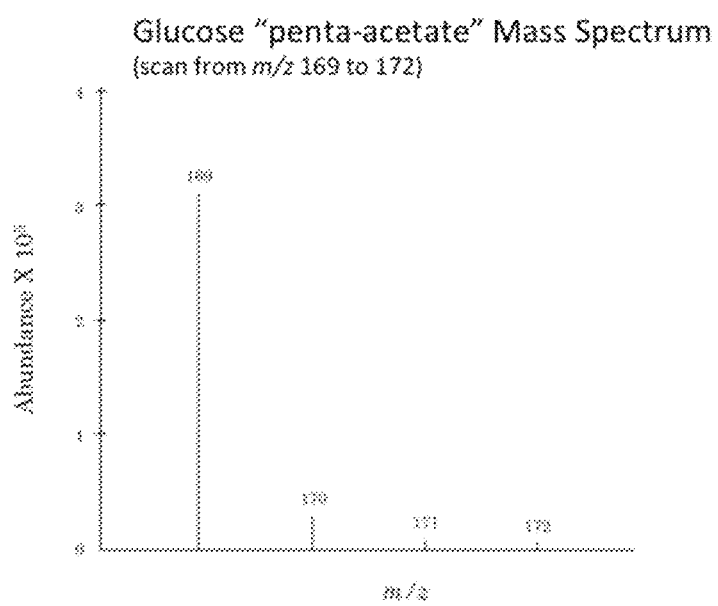
FIG. 8 shows a schematic mass spectrum focusing on the MW 169 and related ions.

FIG. 8 shows a schematic mass spectrum focusing on the 271 ion. Since this ion has lost the hydrogen at carbon 2, it cannot be marked by the GLY pathway. The ratio of 272 to 271 thus represents the enrichment due only to GNG. Since the ion may also exist in a configuration where the hydrogen is still present in the molecule, the estimation of enrichment due to GNG may be modified by a correction factor, in one embodiment 1.0/0.9, because about 90% of the molecules exist in the configuration without the hydrogen at carbon 2.

Figure 9:
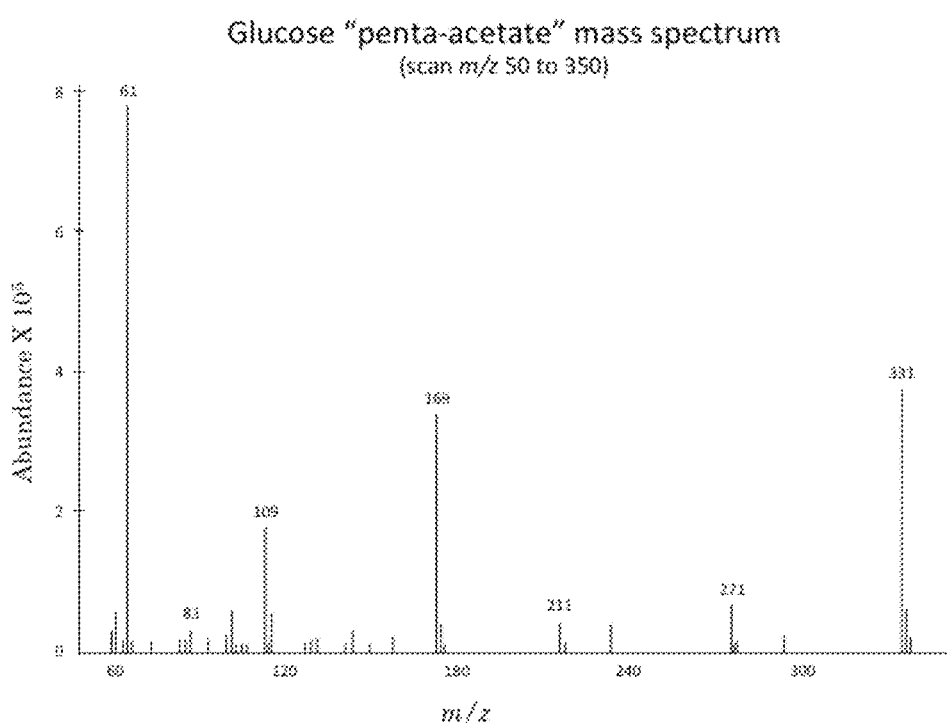
FIG. 9 shows a schematic mass spectrum showing the MW 169, 271, 331 and related ions.

FIG. 9 shows a schematic mass spectrum focusing on the 169 ion. Since this ion has lost the hydrogen at carbon 2, it cannot be marked by the GLY pathway. The ratio of 170 to 169 represents the enrichment due only to GNG. Since the ion may also exist in a configuration where the hydrogen is still present in the molecule, the estimation of enrichment due to GNG may be modified by a correction factor, in one embodiment 1.0/0.65, because about 65% of the molecules exist in the configuration without the hydrogen at carbon 2.

Since we have information on both pathways, we can establish a baseline for the amount of label produced by both the GLY and GNG pathways. The ratio of 332 to 331 represents enrichment by both pathways. When either the 170/169 or 272/271 ratios (or the average of both) is subtracted from this, this yields an estimate of the % of body water labeled, since body water is the starting point for both pathways of glucose genesis. This ratio can be used to confirm the % of body water labeled, in one embodiment. We can also have a % body water label baseline based on the amount of labeled water introduced into the body compared to body weight and/or total body water estimate (generally body water is assumed to be 70% of body weight) in another embodiment. If the ratio of 332/331 minus 170/169 or 272/271 or both differs from this, we can use the average or some other combination of these numbers to establish a baseline for % body water labeled, in another embodiment.

Figure 10:
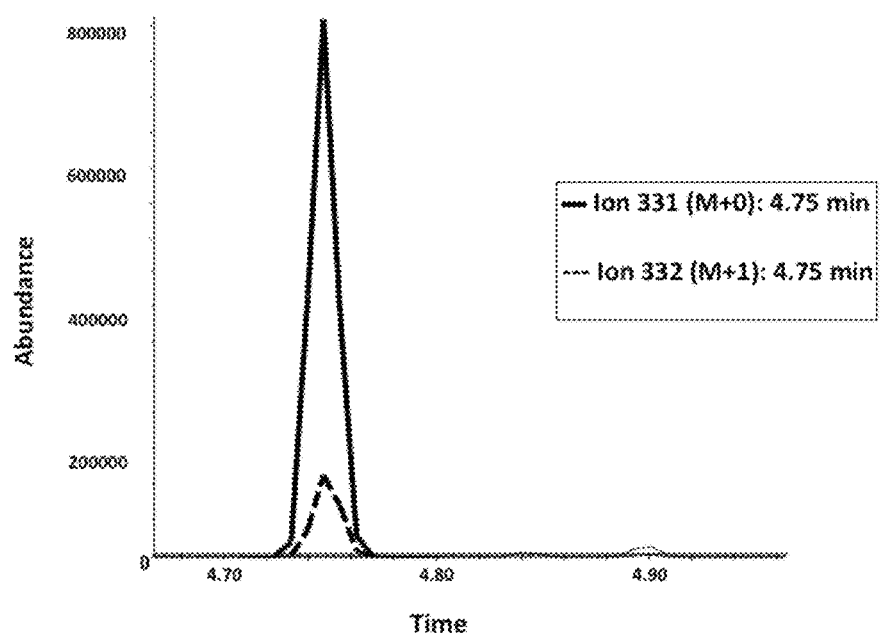
FIG. 10 shows an actual GC/MS spectrum of the current invention, showing peaks corresponding to the selected ion monitoring ("SIM") of the MW 331 and 332 ions, where the intensity of the signal is calculated by integrating the areas under the peaks.

Note that in the above schematic mass spectra, the relative abundance of ions is represented by sharp, one-dimensional lines. The abundances are essentially represented on the y-axis as intensities. In reality, the intensity readings in mass spectra show up as two-dimensional peaks (hopefully, relatively sharp). The signal/intensity/abundance of each ion is generally calculated as the area under the curve of that peak. FIG. 10 shows an actual Selected Ion Monitoring ("SIM") GC/MS spectrum of the current invention, showing peaks for selected ions 331 and 332, In any case, it should be noted that the units of the y-axis are not generally important, as long as the abundance is adequate for good chromatography, since what we care about are intensity/abundance ratios, and the ratios are dimensionless.

In a preferred embodiment, the GC/MS used is the Agilent GCMSD 5973, Of course, other types of GC/MS devices or other types of mass spectrometers such as liquid chromatographs can be used, provided that the enrichment is sufficient to be accurately detected and the molecules, or derivatives and fragments of the molecules representative of the relevant label or labels can be detected. Other types of mass spectrometers such as, but not limited to, three-dimensional quadrupole ion trap, linear quadrupole ion trap, orbitrap, sector, time-of-flight, Fourier transform ion cyclotron resonance or other detectors. Such detectors can be used alone or in combination (called tandem mass spectroscopy), e.g., triple quadrupole, quadrupole ion trap.

The creation of ions can occur by a variety of methods and systems, including, but not limited to, electron ionization ("EI") and chemical ionization ("CI") used for gases and vapors, electrospray ionization, nanospray ionization, matrix-assisted laser desorption ionization ("MALDI"), inductively coupled plasma ("ICP"), glow discharge, field desorption, fast atom bombardment ("FAB"), thermospray, desorption/ionization on silicon ("DIOS"), direct analysis in real time ("DART"), atmospheric pressure chemical ionization ("APCI"), secondary ion mass spectrometry ("SIMS"), spark ionization and thermal ionization ("TMS"). These ionization techniques result in the transformation of the molecule to an ion or multiple fragments of ions. Various chromatographic techniques, for example, gas chromatography ("GC") and liquid chromatography ("LC") can be combined with the mass spectrometer detectors. For LC/MS the interface between liquid phase and gas phase typically uses either nanospray ionization or electrospray ionization.

The invention can also be used with single "purpose-built" mass spectrometers. Distinguished from conventional central laboratory mass spectrometers, purpose-built mass spectrometers, typically are small, single biotechnology application, mass spectrometers that use miniaturized molecular traps operating near atmospheric pressure with small versions of pumps, ionizers, detectors and electronics needed. A handheld version can take a small blood sample so that tests such as % GNG can be easily and routinely sampled.

The invention can use deuterium oxide ($D_2O$) alone, or $D_2O$ with either $D_2$-glucose, or [1-$^{13}$C]glucose tracers administered intravenously upon admission to a hospital intensive care unit ("ICU"), in preoperative preparation or other forms of hospital admittance in order to establish baseline values for glucose Ra, % GNG, and absolute rate of GNG. In a preferred embodiment, assuming when blood glucose is in the normal range without exogenous intravenous glucose supplementation, the use of $D_2O$ alone would be sufficient to yield % GNG as the sole biomarker, and analysis of % GNG alone is a preferred embodiment of the invention.

In short, estimation of % GNG consists of the intravenous administration of tracer or tracers, a small blood sample (small enough in fact for the diagnostic to be used in infants and children), preparation of sample for analysis and mass spectrometry to determine the mass isotopomer distribution of the incorporation of $D_2O$ into the product glucose and the deuterium enrichment of the precursor body water. Our relatively easy, fast and cost effective invention can be easily deployed in hospitals and trauma centers throughout the world. In other preferred embodiments, we can combine % GNG estimates with other analyses ($D_2O$ plus either $D_2$-glucose (2 deuteriums at C-6), or [$1$-$^{13}C$]glucose (glucose with a carbon 13 at C-1), to yield estimates of glucose Ra and absolute rate of GNG. This would give additional information as to the to determine metabolic and nutritional state of the patient.

Expanding on previous methods using mass spectrometry to estimate fractional GNG (20, 30, 44), we propose new stand-alone infusates and diagnostic methods. Using oral and vascular administration of $D_2O$ ($^2H_2O$) and a single, small blood sample, the fractional GNG estimate and deuterium enrichment in body water ($D_2O$ or $^2H_2O$) (precursor) can be simultaneously measured using the ion fragmentation patterns resulting from a single mass spectrum. When the average deuterium (D or $^2H$) enrichment (over glucose carbons 1, 3, 4, 5, 6) is used to determine % GNG, we can call this the "averaging" fractional GNG method of estimation.

When divided by the enrichment of deuterium in body water (i.e., precursor), the fractional GNG estimate (glucose being the product of this pathway), yields the estimation of fractional glucose production from GNG, which we call fractional GNG or % GNG—the terms are used in this invention interchangeably. Instead of performing a separate analysis for the determination of the isotopic enrichment of deuterium in body water, we propose to use multiple fragments that result from the penta-acetate glucose derivative and mass spectrometry. Our invention for the averaging GNG estimate method is to measure the total deuterium enrichment of all hydrogens of glucose and subtracting the enrichment of deuterium on C-1, C-3, C-4, C-5 and C-6, the difference of which results in calculation of the enrichment of deuterium on C-2 of glucose. The enrichment of deuterium on C-2 is equivalent to the enrichment of deuterium in body water. Expressed in another way, enrichment of deuterium on C-2=(1,2,3,4,5,6,6-$H_7$–1,3,4,5,6,6-$H_6$).

Therefore fractional GNG=average (1,3,4,5,6,6-$H_6$)/(1,2,3,4,5,6,6-$H_7$–1,3,4,5,6,6-$H_6$).

The penta-acetate derivative of glucose contains all 6 carbons and 5 acetate functional groups that have replaced the native glucose hydroxyl groups. With methane chemical ionization (CI) and electron impact ionization (EI) the first prominent fragments are mass-to-charge (m/z) 331 and the related naturally occurring isotopomers (m/z 332, 333 and 334). This "331 fragment" contains all the carbons of glucose and all the hydrogens of the glucose molecule (i.e., C-1, C-2, C-3, C-4, C-5, C-6 and H-1, H-2, H-3, H-4, H-5, H-6, H-6 [also can be written as 1,2,3,4,5,6,6-$H_7$] (7 hydrogens total)). The other ion fragments of interest in the proposed method are m/z 169 and its related naturally occurring isotopomers (m/z 170, 171, 172). Similar to the 331 fragment, the 169 fragment also contain all the carbons of glucose, but a different number of related hydrogens (i.e., C-1, C-2, C-3, C-4, C-5, C-6, and H-1, H-3, H-4, H-5, H-6, H-6 [or 1,3,4,5,6,6-$H_6$]). Aspects of our invention are recognition of the loss of H-2 from the 169 fragment, and inclusion of H-2 in the 331 fragment of the penta-acetate derivative of glucose following the administration of $D_2O$ and the process of GNG.

Due to complete hydrogen exchange with body water during the extensive glucose-6-phosphate⇔fructose-6-phosphate isomerization, the enrichment of $^2H$ at C-2 of glucose represents body water enrichment. Using the difference of ion intensities between the two fragments identified above yields both the "average" enrichment of deuterium using ions 169 and 170 [(170/169)/6], plus the body water enrichment calculated from the difference between the M+1 ratio from ions 331 and 332 (332/331) and the M+1 ratio of ions 169 and 170 (170/169). Hence, fractional GNG can be estimated by comparing the deuterium enrichment on C-2 with the "average" enrichment of $^2H$ on a glucose penta-acetate derivative following the administration of $D_2O$.

Alternatively stated, in one embodiment, fractional GNG can be calculated by dividing the "average" $^2H$ glucose isotopic enrichment (the product) by the body water enrichment following administration of water and $D_2O$ (the precursor), see, for example, (20, 30, 58). Restated another way, $^2H$ enrichment on C-2 of a glucose penta-acetate derivative following administration of $D_2O$ is due to both GNG and GLY. However, to reiterate, our new and novel method of measuring % GNG depends on determinations of the positional isomers of deuterium labeled glucose during GNG, an assumption that has been verified independently (20, 30). And any one or more of the GNG enriched carbons can be used to arrive at the % GNG estimate.

To review the formulas relevant to the invention:

$M+1$ ratio=m/z ($M+1/M$); $M$ and $M+1$ represent ion fragments from mass spectrometry The $M+1$ ratio can also be represented as ($M+1$/Sum ($M+(M+1)$)). For example using ion fragment 331, $M+1$ ratio=332/(331+332).

Mole Percent Excess ("MPE")=$M+1$ ratio$_{sample}$–$M+1$ ratio$_{background}$; sample is blood sample acquired after administration of $^2H_2O$, and background is blood sample acquired upon admittance to hospital and before administration of $D_2O$. $M+1$ ratio (332/331)–$M+1$ ratio (170/169)= body $^2H_2O$ $M+1$ ratio (170/169)$_{sample}$–$M+1$ ratio (170/169)$_{background}$=Total MPE Total MPE/6=average $^2H$ enrichment of C-1, C-3, C-4, C-5, and C-6 blood glucose penta-acetate derivative Fractional GNG=average $^2H$ enrichment/body $^2H_2O$ In a preferred embodiment, the method of invention is comprised of three independent parts. Part 1 comprised of two sub-parts, (1A) administering $D_2O$ to an ill or injured patient or to a healthy control in who GNG needs to be measured, and (1B) measure the glucose penta-acetate ion fragmentation patterns by mass spectrometry, as described above.

Sub-Part 1A

At the start of treatment, e.g., on admission to a research laboratory, hospital or clinic for ill or injured patients, or research laboratory, for healthy subjects and scientific study, and before administration of $D_2O$, a background blood sample should be drawn and prepared for analysis. The background sample is useful because, depending on a patient's dietary and environmental history, small and variable amounts of $^2H$ and $^{13}C$ isotopomers naturally occur in body water, blood metabolites and other body compartments. After this background blood sampling and analysis, a constant infusion of deuterium oxide will commence (with or without a bolus depending on the whether % GNG needs to be assessed in the first several hours of admission). Because the deuterium oxide equilibrates with the body water, a desired enrichment can be achieved and maintained throughout the entire hospitalization period.

The desired isotopic enrichment of body water (in one embodiment about 0.3-0.5%, or adequate for ion intensity comparisons from the utilized method of mass spectrometry) will be adjusted by the constant infusion of $D_2O$ and verified by the determination of deuterium enrichment on C-2 (as described above using the difference in ion intensities between ion fragments 331 and 169). Alternatively the determination of body water enrichment can be determined by isotope ratio mass spectrometry (31, 66) or using an isotopic exchange with acetone method (81). Then, when needed and as frequently as necessary, a small blood sample can be drawn to determine fractional GNG on an ongoing/dynamic basis. As nutritional support is augmented using the following parts of the invention, the fractional GNG will be controlled, such as within the target range (20-25%) in a preferred embodiment, varied to mimic a normal daily circadian pattern, or varied to yield any particular % GNG ranging from 0 to 100% in other embodiments.

The frequency of blood sampling following $D_2O$ administration, the subsequent calculation of % GNG, and adjustment of enteral and parenteral nutrition is limited by the time needed for analysis. Given current technology, a 2-hr frequency should be practical. However, as technology advances, the frequency of sampling may increase. In a busy hospital setting, morning, noon and evening sampling may be necessary to estimate % GNG and other biomarkers.

Sub-Part 1B

The analysis of the data derived from the analytical process in Part 1 determined from the mass isotopomer distribution of deuterium incorporation into glucose yields the rate of GNG, which can also be understood as the % of Ra glucose derived from GNG precursors (mainly lactate). This is referred to as fractional GNG or % GNG. Fractional GNG is proportional to the rate of glucose production. In a normal resting person, % of total glucose production to support the brain approximates 25%, a very high percentage considering the mass of the brain in comparison to the rest of the body. Blood glucose demands increase in injured persons regardless of the site of injury, and the balance of glucose Ra from GLY and GNG varies depending on nutritional state, time and metabolic needs of various body tissues. Paradoxically, following brain injury, cerebral glucose uptake is stunned and diminished, however, the % of cerebral glucose uptake from GNG rises, as has been observed by the inventors and other researchers, in studies to be published in the coming months.

In healthy, uninjured persons the % GNG can fluctuate between ~10% (over fed), to ~20-25% (appropriately nourished) to as high as ~90% (in undernourished and catabolic patients). Our observations show that % GNG approximates 70% for TBI persons in the ICU, as has been observed by the inventors and other researchers, in studies to be published in the coming months.

Importantly, even though the % GNG will follow a circadian fluctuation in a traumatized or critically ill patient; this fluctuation can be minimized by the provision of nutritive support to achieve a normal (20-25) % GNG, indicative of normal metabolic and nutritive states. By this means, "exquisite" glycemic control and Ra glucose, without the use of conventional or intensive insulin therapy, can be achieved, which may be of critical benefit to the patient.

In describing % GNG it needs to be understood that % GNG is a variable that can have physiological range of 0 to 100%. Based on our work as well as that of others, the stated target range of 20-25% in healthy post-absorptive individuals, is a biomarker for adequate nutrient delivery in an ill or injured patient or other individual incapable of taking adequate macronutrient nutrition, as defined by the Harris-Benedict (32) or Institute of Medicine equations (8, 51). In a preferred embodiment of the invention, nutrition is provided so that % GNG is between about 15 and 30%. In another preferred embodiment of the invention % GNG of about 20-25% is aimed for based on studies on healthy young individuals 3-4 hours after having eaten (3, 24, 26, 27, 58, 73).

Part 2

Part 2 articulates the metabolic and nutritive state, also known as body energy state (76) of the patient. For Part 2 the acquisition of the mass isotopomer distribution of the deuterium and hydrogen content in the body water and the glucose, taking into consideration the natural occurrence of isotopes of carbon and other atoms with naturally occurring isotopes, consists of selective ion monitoring ("SIM") of the mass to charge ratio (m/z) of the ions of interests coupled with an integration of the SIM to deduce the response factor associated with the abundance of the ions of interests as they relate to the precursor and product relationship.

The invention also includes a method and system to compare the precursor and product relationship based on the patient's baseline measurement and the daily (or multiple daily) measurements taken from the patient. The invention, in a preferred embodiment, has a database that informs the basis from which the nutritional status was evaluated and the prescription of nutritional support was determined. With the additional process of part 1, the database will contain variables for the relevant ions (e.g., 331, 332, 272, 271,169, 170) to calculate fractional GNG and body water enrichment as it relates to infusion of the tracer deuterium oxide and the precise, prescription nutritional support. As well, the system will contain non-identifiable data on patients, the severity of injury on entry into the study, the initial % GNG, the enteral and parenteral nutrition provided, and patient outcomes.

It will be appreciated that many of the described methods can be intermediated and implemented automatically by a computer, or special-purpose hardware, or some combination of both, as such systems are well known in the art. Specialized software or hardware of the invention could read the intensity of signals provide my mass spectra and automatically calculate the ratios and other important data to give a reading of fractional GNG. Such readings could automatically be stored in databases or computer memory and presented to users in various visual forms. The software could also make recommendations as to feeding protocols and times, frequency of patient sampling, or simply carry out these methods automatically.

The invention as such can be implemented on any suitable computer system. A typical, general purpose computer system suitable for implementing the present invention includes any number of processors that are coupled to memory devices including primary storage devices such as a read only memory, random access memory and hard drives. Any one of many data and database architectures can be used to store and retrieve methods, protocols and recommendation, to store data, and to communicate with server side assistance through the Internet and other networks.

A hardware system may be specially constructed for the required purposes, or it may be a general-purpose computer, such as a server computer or a mainframe computer, selectively activated or configured by a computer program stored in the computer. The processes presented above are not inherently related to any particular computer or other computing apparatus. In particular, various general-purpose computers may be used with programs written in accordance with the teachings herein, or, alternatively, it may be more convenient to construct a more specialized computer system to perform the required operations.

Such a general-purpose computer system suitable for carrying out the processing in accordance with one embodiment of the present invention can be a server computer, a client computer, or a mainframe computer. Other computer system architectures and configurations can be used, made up of various subsystems described below, includes one or more microprocessors (or central processing units). Using instructions retrieved from memory, the microprocessor controls the reception and manipulation of input data, and the output and display of data on output devices.

Part 3

Part 3 relates to nutritive methods, formulations and amounts. With the prescription of medicine determined following parts 1 and 2 dictated by the invention for each patient, the attending physician shall administer the level of nutritive support to administer to each patient to normalize the % GNG. Further, the attending physician or other health care professional shall utilize information from continual determinations of GNG and nutrient delivery following application of parts 1 and 2 of the invention for each patient as they recover or as conditions change. The invention will prescribe feeding protocols for the patient, as follows, based on general nutritional concepts described in (8, 51).

(A) A preferred form of treatment will consist of the intravenous infusion of the gluconeogenic precursor, including any of the following in combination or alone: L-(+)-lactate salts, other lactate compounds, L-(+)-pyruvate salts, other pyruvate compounds, L-(+)-lactate alone, lactate plus other amendments included. Lactate, pyruvate and similar nutritional molecules are herein referred to as monocarboxylate compounds ("MCC"). The metabolic precursors of glucose in the GNG pathway are herein called GNG precursors. These include many MCCs, such as those listed herein, as well as other compounds, such as some amino acids (e.g., alanine) and glycerol compounds.

These nutritive formulations are referred herein as cocktails, infusions, formulations, MCC cocktails and GNG precursor cocktails. To provide nutritive support and reverse body catabolism to anabolism following trauma or chronic illness, the rate of MCC infusion would range from high (13) to low (13) as governed by the individually measured % GNG and glucose appearance rates:

High (Maximum) MCC Cocktail infusion rate (mg/min)=glucose Ra (mg/min)   A1

Low (Minimum) MCC Cocktail infusion rate (mg/min)=glucose Ra (mg/min)×(% GNG)=absolute rate of GNG   A2

In its simplest form, the MCC cocktail would be sodium-L-(+)-Lactate prepared by titrating L-(+)-Lactic acid with NaOH (24, 52, 55-57). Briefly, the MCC infusion cocktail is prepared by mixing 30% L-(+)-lactic acid solution (e.g., Sigma) in 2 N NaOH to pH 4.8, The invention, in one embodiment, specifies an initial infusion rate would deliver 11-50 (micro Moles per kg of body weight per minute) µMoles/kg/min, with maintenance infusion rate targeting blood lactate concentration of 3.5-4.5 mM. Higher blood lactate levels (6 mM) have been seen without ill effects (57, 71). Consistent with section methods described above, assuming a formula weight of 112 mg/mMol for sodium lactate, an infusion rate of 11 µMoles/kg/min would deliver the mass equivalent of 1.0 mg/kg/min of glucose, an infusion rate of 23 µMoles/kg/min of sodium lactate MCC would deliver the mass equivalent of 3 mg/kg/min glucose, whereas an infusion rate of 50 µMoles/kg/min would deliver the mass equivalent of 4.5 mg/kg/min of glucose. Ideally, the MCC is prepared from highest purity materials, is pathogen free, certified for human pharmaceutical use and is delivered into a large central vein, but peripheral vein can be used if administered with physiological saline to minimize osmolality and pH effects at the infusion site that might provoke phlebitis of hemolysis.

In one embodiment, the starting MCC infusion rate is approximately 3 mg/kg/min, or in an alternate embodiment, 100% of glucose Ra, as has been observed by the inventors and other researchers, in studies to be published in the coming months. In one embodiment, this can be done even without estimating % GNG, Ra glucose or other biomarkers. This route and amount of vascular lactate administration has been shown to be safe (55-57, 71). The amount also corresponds to the average empirically determined Ra glucose in TBI patients (74), as has been observed by the inventors and other researchers, in studies to be published in the coming months.

The invention provides for adjusting the nutrition, including MCC infusion rates, such that a target % GNG is achieved. To some, results of studies of the extent of gluconeogenesis in humans might seem quite variable; however, if results are viewed from the context of subject time since last eating, then a clear pattern emerges: GNG is suppressed as nutrients enter the gut, portal and circulation (e.g., 0-15% of glucose Ra), and 20-25% of glucose Ra 3-4 hr after a mixed, CHO (carbohydrate) containing meal, and the percentages rises continuously thereafter (74).

(B) An alternative and also preferred form of treatment will involve Procedure A plus either (B1) enteral nutrition via nasal gastric or nasal jejunal tube, or parenteral nutrition (B2) via intravenous catheter. If these, Method B1 is useful because nutrients will enter the stomach and reach intestines, portal circulation and liver, thereby eliciting physiologically appropriate and anabolic local intestinal and long neural endocrine reflexes as well as general endocrine responses with signals reaching the liver, pancreas, muscles, heart, adipose, and brain including hypothalamus regarding the presence of appropriate nutritive energy support (79).

(B1a) The clinician shall proceed as in (A), above, but, as well, provide enteral nutritive support according to various protocols, such as the Appropriate Macronutrient Distribution Ranges ("AMDR") as defined by the Institute of Medicine ("IOM"). These AMDR ranges are: carbohydrate in the range of 45-65%, protein in the range of 10-35% and fat in the range of 20-35%, with total daily energy input as determined by the IOM equations for men and women (8, 51) assuming no physical activity, but a 10% increase in total daily energy expenditure ("TEE") to support hypermetabolism of trauma and cover energy needs for tissue repair such that physical activity level ("PAL") (8, 51)=1.1:

Men: TEE=1864−9.72×age [yr]+PAL×(14.2×weight [kg]+503×height [m])

Women: TEE=1387−7.31×age [yr]+PAL×(10.9× weight [kg]+660.7×height [m])

(B1b) The clinician shall proceed as in (A), but as well provide enteral nutritive support from various protocols, such as according to the Appropriate Macronutrient Distribution Range ("AMDR"s) as defined by the Institute of Medicine (51), and that energy is delivered according to the Harris-Benedict Equations (32):

Men: TEE=66.473+13.7516 *W* [kg]+5.0033 *H* [*cm*]− 6.7550 Age [yr]

Women: TEE=655.0955+9.5634 *W* [kg]+1.8496 *H* [*cm*]−4.6756 Age [yr].

(B2) The clinician shall proceed as in (B), but nutrients will be administered into the blood via an indwelling catheter. Monitoring and adjustment of MCC and macronutrient infusion rates will be similar to (A) and (B1).

(C) Another embodiment of the invention relies on robust, scientifically determined underpinnings of the metabolic and GNG responses to trauma, including neurotrauma, as has been observed by the inventors and other researchers, in studies to be published in the coming months, and is to be regarded as an emergency procedure when isotopes and analytical equipment are unavailable and the patient needs to be sustained until relocation to an appropriately equipped facility.

(C1a) The clinician shall commence intravascular infusion of Na$^+$-L-(+)-Lactate at the rate of 3 mg/kg/min plus enteral nutritive support according to the AMDRs and TEE estimates as given by the Institute of Medicine ("IOM") (8, 51).

(C1b) The clinician shall commence intravascular infusion of Na$^+$-L-(+)-Lactate at the rate of 3 mg/kg/min plus enteral nutritive support according to the AMDRs and TEE estimates as given by Harris and Benedict (32).

(C1c) The clinician shall commence intravascular infusion of Na$^+$-L-(+)-Lactate at the rate of 3 mg/kg/min plus parenteral (intravascular) nutritive support according to the AMDRs and TEE estimates as given by the IOM (8, 51).

(C1d) The clinician shall commence intravascular infusion of Na$^+$-L-(+)-Lactate at the rate of 3 mg/kg/min plus parenteral (intravascular) nutritive support according to the AMDRs and TEE estimates as given by the Harris-Benedict equations (32).

(D) Another embodiment of the invention also relies on robust, scientifically determined underpinnings of the metabolic and GNG responses to trauma and is to be regarded as an emergency procedure when isotopes, analytical equipment and MCCs are unavailable and the patient needs to be sustained until relocation to an appropriately equipped facility. Such locations could include, for example, a battlefield or a rural setting.

(D1a) In a facility unequipped to determine % GNG the clinician shall commence intravascular infusion of D-Glucose at the rate of 1-2 mg/kg/min and enteral nutritive support according to the AMDRs and TEE estimates as given by the IOM (8, 51). The inventors have seen a rate of 3 mg/kg/min in TBI patients, as has been observed by the inventors and other researchers, in studies to be published in the coming months. However, experience teaches that it is difficult to maintain the desirable [glucose] in severely injured patients (78). In severely injured patients giving exogenous glucose (usually in the form of dextrose) may induce hyperglycemia thereby eliciting an insulin response or the need to administer insulin due to undesirably high [glucose].

This undesirable process can be described as a pattern of clinicians to clumsily trying to ride a "metabolic roller coaster" of intravenous dextrose followed by insulin and yet again dextrose, and the current invention can eliminate this problem. Importantly, while spending time, effort, resources and attention by managing [glucose] in patients by alternately adjusting infusion rates of dextrose and insulin, the clinician obtains little useful information or meeting patient nutrient needs. The current invention will enable clinicians to meet patient nutrient needs and serves to save clinician time and effort and releases clinicians from the responsibilities associated with managing the aforementioned metabolic roller coaster.

(D1b) The clinician shall commence intravascular infusion of D-Glucose at the rate of 1-2 mg/kg/min and enteral nutritive support according to the AMDRs and TEE estimates as given by Harris and Benedict (32).

(D1c) The clinician shall commence intravascular infusion of D-Glucose at the rate of 1-2 mg/kg/min and parenteral (intravascular) nutritive support according to the AMDRs and TEE estimates as given by the IOM (8, 51).

(D1d) The clinician shall commence intravascular infusion of D-Glucose at the rate of 3 mg/kg/min and parenteral (intravascular) nutritive support according to the AMDRs and TEE estimates as given by the Harris-Benedict equations (32).

(D1e) If enteral or parenteral support is unavailable, the clinician shall commence intravascular infusion of D-Glucose at the rate of 3 mg/kg/min which is the empirically derived best estimate of body glucose flux following a TBI or other injury, illness or situation, as has been observed by the inventors and other researchers, in studies to be published in the coming months. This elevated value of glucose flux that occurs after TBI or other injury, illness or situation, is indicative of a "hypermetabolic" state would be in contrast to the depression in glucose flux as might occur in a "hypometabolic" state, such as advanced aging (see below, vide infra).

In a preferred embodiment, nutritive support treatment targets are % GNG 20-25%. In another preferred embodiment plasma [glucose] is targeted as 5-7 mM. In another preferred embodiment, plasma [lactate] is targeted as 3-4 mM. These targets can be achieved by adjusting MCC, enteral and parenteral administration rates either singularly, or in combination. However in methods C and D, % GNG will not be known. In these cases, in addition to adjusting MCC, enteral and parenteral administration rates, insulin therapy may be indicated above a certain [glucose] such as 7.8, or below 5.6 mM (75).

The robust nature of the GNG response to the stresses of injury can be supported by provision of an MCC, that can be comprised of one, or combinations of the following: sodium L-(+)-lactate, arginyl lactate, glycerol, glycerol tri-lactate, sodium L-(+)-pyruvate, arginyl pyruvate, glycerol tri-pyruvate, glycerol tri-acetate, β-OH-butyrate or acetoacetate [in which all monocarboxylate enantiomers are L-(+)-enantiomers], or mixtures thereof in which the relative amount of any single constituent could range from 0-100%. As well, embodiments of a MCC cocktail could include $Ca^{++}$, $Mg^{++}$, and $K^+$-salts of lactate, pyruvate, alanine, β-OH-butyrate, acetoacetate, etc., as all are salts of monocarboxylic acids. However, sodium ion ($Na^+$) is the main cation in plasma, normally 145 mM, other cations are far less abundant in plasma. For instance, normal values for $K^+$, $Ca^{++}$, and $Mg^{++}$ are, respectively, 4, 2.5 and 1.5 mM. Hence, a mixture of inorganic lactate salts comprised of $Na^+$, $K^+$, $Ca^{++}$, and $Mg^{++}$ would be given in the ratio of 145, 4, 2.5, and 1.5, In this embodiment of invention, the main anion would be lactate, but phosphates ($PO_4^{3-}$), hydrogen phosphate ($HPO_4^{2-}$) and dihydrogen phosphate ($H_2PO_4^-$), in the amount of 1.0 mEq would be provided as well. Because $Na^+$, $K^+$, $Ca^{++}$, $Mg^{++}$, and $H_2PO_4^-$ are present in the plasma of healthy individuals at levels of 145, 4, 2.5, 1.5, and 1.0 milliequivalent per liter (mEq/l, this particular embodiment of MCC could be termed "Sanguisal" from the Latin words for blood (sanguis) and salt (53). The provision of sodium and other cations as a means to deliver lactate anions in an MCC has the advantage of reducing brain swelling following TBI, as has been observed by the inventors and other researchers, in studies to be published in the coming months and (15) as well as providing nutritive support to intensive care patients following trauma (70).

As an alternative to Sanguisal-L that uses lactate as the major anion (vide supra), Sanguisal-P will involve the use of pyruvate (P) as the major anion, while at the same time maintaining the above-stated levels of cations {$Na^+$, $K^+$, $Ca^{++}$, $Mg^{++}$, and $H_2PO_4^-$ as are present in the plasma of healthy individuals: 145, 4, 2.5, 1.5, and 1.0 mEq/l}. Like it's counterpart lactate, pyruvate is the precursor to lactate in glycolysis. Further, pyruvate is an oxidizable fuel and GNG precursor whose metabolism may affect cell redox status if converted to lactate. Although typically present in 1/10 or lesser concentration compared to lactate, pyruvate has been introduced into the systemic circulation of large mammals in which the circulation has been interrupted to mimic cardiac arrest (61-63, 68). In such cases 100% pyruvate infusion raises the circulating pyruvate level, but more so, the circulating lactate level achieving a circulating L/P of 2-3 (69). None the less, because of its chemical structure, pyruvate has the advantage over lactate of serving as an antioxidant in the myocardium subjected to reperfusion injury, and, by extension exogenous pyruvate my also serve to scavenge free radicals in the brain after blood flow is interrupted.

A problem with regard to the use of Sanguisal-P, in contrast to the -L form, is that in circulation pyruvate is rapidly converted to lactate due to the effects of lactate dehydrogenase in red blood cells and the lung parenchyma (41). Hence, for the antioxidant properties of pyruvate (48), the optimal site of Sanguisal-P infusion would be in the carotid artery or ascending aorta. Still, by the ability to infuse mixtures of Sanguisal-L and Sanguisal-P into the systemic circulation, ascending or carotid artery, the clinician would have the opportunity to affect redox status in an injured brain. However, because carotid or ascending catheterization is uncommon even in the ICU, systemic solutions of a very low L/P ratio (i.e., high P/L) such as infusion of 100% Sanguisal-P, or a mixture of Sanguisal-P/Sanguisal-L of 2.0 (L/P=1/2 in the infusate), would serve to raise the arterial level of pyruvate relative to that of lactate.

It should be noted that one issue with aqueous pyruvate-containing solutions is the spontaneous degradation of pyruvate and the accumulation of unintended and possibly toxic substances in aqueous conditions. Accordingly, the manufacturing and storing Sanguisal P and Sanguisal L-P mixtures needs to be anhydrous. Water (pure and sterile) can then be added to the formulation immediately before delivery to the patient.

In using Sanguisal-L, Sanguisal-P, or other sodium salts of lactate or pyruvate the assumption is that the patient to be supported has normal renal function and is capable of managing the sodium load. In the event that the patient does suffer renal failure, then the use of Sanguisal or other sodium-based salts will need to be reduced to the levels where normal sodium, potassium and other plasma cations are in the normal range. In this case also, substrate availability in patients can be maintained by combinations of intravenous Dextrose (a synonym for glucose), with and without insulin, and enteral nutrition as described in section D, above. Still, however, % GNG will serve as the biomarker around which to provide enteral and parenteral nutrition.

Alternative Methods to Estimate % GNG

The invention is comprised of a three-part process to assess the metabolic status and deliver macronutrient energy to an ill or injured human or other mammal. The first part is to estimate the % GNG, the favored method is to utilize deuterium oxide ($D_2O$) alone, or $D_2O$ with either $D_2$-glucose, or [1-$^{13}$C]glucose tracers administered intravenously upon admission to a hospital ICU (20).

One advantage of the new method is that the tracer needs to be given once that will suffice for measurements of GNG to be made daily for several days and a constant infusion can be started to offset the dilution of the enrichment of the deuterium oxide caused by intake of fluids. However, we have used primed-continuous infusions to measure glucose recycling or lactate incorporation lactate into glucose. The former method (glucose recycling) requires using $D_2$-glucose (that does not involve carbon recycling, and a $^{13}$C-glucose tracer (e.g., [1-$^{13}$C]glucose) in which the carbon recycles (26, 27). In this carbon-recycling method, % GNG= (100) Ra Glucose (from $^{13}$C-glucose)–Ra Glucose (from D2-glucose)/Ra Glucose (from $D_2$-Glucose). Disadvantages of this method are that tracers will need to be given continuously over days, perhaps leading to weeks, and that assumptions need to be made over the extent of carbon isotope dilution in the Krebs (tricarboxylic acid) Cycle (37, 38).

Another method also uses deuterium oxide and measures the deuterium incorporation on glucose carbons using the mass isotopomer analysis technique with the aldonitrile penta-acetate and methyloxime-trimethylsilyl derivatives (42).

Another alternative method also uses deuterium oxide but measures the enrichment at carbon 2, 5, and 6 of glucose using the HMT (hexamethylebetetramine) derivative. Disadvantages of this method are the complexity in preparing the derivative (44, 45).

Another alternative method involves primed-continuous infusion of $D_2$-glucose (and a $^{13}$C-lactate tracer (e.g., [1-$^{13}$C]lactate) (3) in which the carbon from lactate recycles to glucose. Disadvantages of this method are that tracers will need to be given continuously over days, perhaps leading to weeks, and that assumptions need to be made over the extent of carbon isotope dilution in the TCA Cycle.

Another alternative method involves the primed-continuous infusion of $H^{13}CO_3^-$ (i.e., $^{13}$C-bicarbonate) that will be fixed as the result of isotopic equilibration during the process of gluconeogenesis (37, 65). Disadvantages of this method are the tracer needs to be given continuously over days, perhaps leading to weeks. Again, the method relies on assumptions on the extent of carbon exchange during GNG, with the extent of isotopic dilution subject to metabolic state of the individual (38).

Another alternative method involves the use of mass isotopomer distribution analysis (MIDA) using a labeled glycerol precursor. Disadvantages of this method include the large amount of tracer needed to make the measurement. (35, 58).

Another alternative method involves the use of [U-$^{13}$C] glucose (72). This method was enhanced to the "Reciprocal pool model" by (34). Disadvantages of these methods are that the tracers need to be given over days and potentially weeks.

Still other methods for assessing GNG in vivo do not involve isotopomer detection via mass spectrometry, but instead rely on nuclear resonance spectrometry (MRS, or NMR), e.g., (46). The literature on isotopomer detection via MRS is less extensive, but the method may prove to be more sensitive, for instance extending the time between frequency of dosing with $D_2O$ to estimate GNG, or % GNG. However, the large amount of deuterium oxide needed for the measurement may lack efficacy.

In a preferred embodiment to measure fractional GNG, $D_2O$, also called deuterium oxide or heavy water, either alone or in combination with [6,6-$^2$H]glucose (i.e., DD-glucose or $D_2$-glucose) or [1-$^{13}$C]glucose) (20), is administered intravenously. Then, after a set amount of time a blood sample can be obtained, and the mass isotopomer distribution in the blood sugar glucose produced from the heavy water precursor can be analyzed to determine the percentage contribution of gluconeogenesis (% GNG) to the total rate of hepatic plus renal glucose production, alternatively termed glucose appearance (Ra glucose) that can be determined from the isotopic enrichment ("IE") of $D_2$-glucose in blood. Beyond the isotope tracer method noted by example for measurement of % GNG, other methods also exist to determine % GNG, see below (3, 26).

The major GNG precursor is the monocarboxylate, 2-hydroxy-propionate (also known as lactate) (3, 40, 54), which is also a major energy substrate for most body tissues (5-7) including the brain (28, 33, 64). As well, to lesser extents, the salts of other monocarboxylic acids are also gluconeogenic precursors; these include: pyruvate, acetate, acetoacetate, β-hydroxybutyrate, and related compounds, see below. Because at physiological blood pH (about 7.4) monocarboxylic acids (lactic, pyruvic, acetic, β-hydroxybutyric, acetoacetic acids, etc.) will be dissociated to protons and respective anions, here we refer the monocarboxylate anions lactate, pyruvate, acetate, acetoacetate, and β-hydroxybutyrate.

According to the invention, in one embodiment, the fractional GNG is used to determine nutritive support rate to achieve preferred glucose Ra and fractional GNG. For example, an injured patient may have an increased metabolic rate (hypermetabolic) and thus need both glucose and GNG precursor support. By contrast, an aging or chronically ill patient may have a depressed whole body metabolic rate (hypometabolic), but still an elevated need for GNG precursors without glucose support. Even with knowledge of [glucose], which is commonly measured, but without a clear picture of the fractional GNG rate (our biomarker for the metabolic and nutritive state of the patient), a clinician may not recognize that the patient is in a catabolic state and is degrading essential body stores to provide the precursors and energy for GNG.

Conversely, a clinician might induce a nutritional state that renders the patient overfed by administering too much nutrition because a lack of knowledge of the underlying metabolic and nutritional status of the individual patient. An overfed patient can result in significant metabolic stress and may result in complications including prolonged mechanical ventilation, infection risk, delayed hospital discharge and even increased morbidity (29, 47). Indeed, without knowledge of the fractional GNG and based on false assumptions of previous art, a clinician may be unaware of the body's attempt to supply glucose from gluconeogenesis, and, in fact, the clinician may inadvertently act to suppress GNG (78).

Application of the Invention to Various Injuries and Illnesses

By way of describing importance of our method for providing nutritive support to injured patients is to describe the condition of TBI (also known as intracranial injury). Such injuries occur when an external force suddenly impacts, and causes injuries to the brain (15). Often the mechanism of injury produces two, or more lesions, one a laceration or contusion at the site of impact or cranial penetration, and the other a contralateral contusion injury if the force of impact is sufficient to accelerate the brain such that it forcibly contacts the cranium at a vector directed by the initial impact. TBI can be classified based on severity, mechanism (closed or penetrating head injury), or other features, e.g., occurring in a specific location or over a widespread area (15, 28). Head injury usually refers to TBI, but is a broader category because it can involve damage to structures other than the brain, such as the scalp and skull (15). TBI is a major cause of death and disability worldwide, especially in children and young adults and the elderly. Causes include falls, vehicle accidents, and violence.

Typically, following severe TBI, patients are unconscious in a coma, are on life support in a hospital intensive care unit ("ICU"), and have less than 100% chance of surviving and less than 100% chance of regaining pre-injury cerebral functions if they do survive (28). More and more, sports related concussions in American football and other activities, involving loss of consciousness, or other neurological symptoms such as dizziness, nausea, the patient "seeing stars" and behavioral changes are becoming recognized as mild forms of TBI. Especially of concern is growing recognition of the frequency and severity of sports-related concussions to student athletes, still undergoing neural development, and who are particularly sensitive to repeated cerebral injuries. And finally, another source of TBI occurs to soldiers concussed, and injured in the field as the result of improvised, and other explosive devices.

Given this unfortunate background of TBI following vehicle accidents, falls, violence, sports and warfare, our method of determining the rate of GNG following trauma and restoring the rate to normative levels is becoming increasingly important because of the frequency and severities of injuries.

The description includes examples of patient treatment following trauma and chronic illness. The invention includes, methods for managing those extreme and other cases and instances when assessment of BES, diagnosis and treatment are appropriate. Such examples include, but are not limited to assessing BES of patients or others before and after surgery, before and after drug treatment or dietary intervention, or any situation in which knowing, or standardizing BES is essential for determining outcome of any treatment, or establishing the effect of said treatment on humans or other mammals.

GNG is part of normal physiology that includes the "fight-and-flight" response to emergency situations that is well-known in the art, see for example the classic work of Selye (67), and the reference books by Cannon, W. B. "The Wisdom of the Body" (17) and Brooks (12)). In both healthy and uninjured persons, gluconeogenesis works to maintain blood glucose concentration, or glycemia, in the normal range in the early morning hours after the previous evening's meal has been digested and nutrients cleared from the blood, and when the maintenance of glycemia depends on GNG (54). Commonly stated examples given to illustrate importance of the fight and flight response are evolutionary in nature, such as the need to flee predators, or catch large game animals.

While interesting, such examples are remote from contemporary human experience, but injuries and illnesses persist in society and are associated with comorbidities, including nutrient deprivation. Seen in the context of contemporary fight and flight responses, following TBI and other forms of trauma of the critically ill or injured patient the need to provide blood glucose is paramount because glucose is an essential fuel for the brain, as has been observed by the inventors and other researchers, in studies to be published in the coming months, and other tissues such as nerves, red blood cells and the kidneys (8, 51). Indeed, the dietary reference intake ("DRI") for total daily carbohydrate ("CHO") consumption was established based on the glucose needs for the brain (8, 51). Therefore, not only is the total body needs for glucose increased following TBI, but also elevated is the rate of gluconeogenesis from lactate and other GNG precursors, as has been observed by the inventors and other researchers, in studies to be published in the coming months.

The body's need for GNG is increased following TBI, and mimics the starvation state in which body tissues are cannibalized (catabolized or degraded), as is well-known in the art, for example see the textbook by Brooks (12). This pathway supplies byproducts of carbohydrate (e.g., lactate and pyruvate), amino acids (e.g., alanine), and fats (e.g., glycerol and ketones such as β-hydroxy butyrate and acetoacetate) (16). Of these, lactate is by far the most important GNG precursor, easily seen during exercise when blood lactate concentration is elevated (3-5, 7). Crucially, even though GNG provides a short term, fight- and-flight response to the emergency need for a glucose supply to the brain, nerves and other glucose requiring tissues, the price of GNG is to sacrifice (catabolize) essential body substances and tissues. Crucial also is the realization that the basic needs for glucose and other macronutrients by glucose-requiring tissues continue unabated whether those tissues are traumatized, or not. Hence, key underlying concepts of our invention are that glucose and other macronutrients are required, always, that the requirement is the same as normal or increased after trauma, and that the rate of GNG is a critical marker of body tissue catabolism following injury, and alone can be used to direct nutritional treatment.

Derived from such knowledge gained through innovative technology are clinical procedures and materials to support glucose Ra while minimizing % GNG, because GNG is the best real-time measure of body wasting. As well, we assert that these methods have application beyond TBI to the treatment of trauma and chronic and infectious illnesses, in general, because the same methods support the body corpus overall that is comprised of injured and non-injured tissues all requiring nutrient supply.

For a traumatized patient, cachexia, or body-wasting syndrome, is a problem because basal metabolic rate is elevated, but the person is unable to eat. Body weight loss, muscle atrophy and weakness and fatigue result leaving a person diminished even if they survive. In addition to trauma, other conditions and illnesses of life are accompanied by loss of appetite and cachexia. These include aging, infectious diseases (e.g., tuberculosis and AIDS), chronic diseases (chronic obstructive lung disease, multiple sclerosis and congestive hear failure), cancer and some autoimmune disorders. Regrettably also, exposure to environmental toxins (e.g., mercury) can result in cachexia, and occasionally there are some who are unable to access food and are starved. All such sick individuals and chronically ill patients who are unable to ingest adequate macronutrients to maintain body requirements, let alone restore health would also benefit from treatment by the invention we describe.

It has long been recognized that patient care in the ICU necessitates the monitoring of blood glucose concentrations due to the stress from critical illness. Some have identified insulin resistance and unsuppressed gluconeogenesis (i.e., when negative feedback from rising blood [glucose] fails to down regulate GNG) that results in the required monitoring of blood glucose in over 90% of ICU patients (83). Additionally, various attempts to control blood glucose concentration including hyperglycemia with blood glucose concentration of 180-215 mg/dL is considered beneficial.

Conversely, others have attempted to regulate blood glucose concentration to values between 80 and 110 mg/dL in an attempt to maintain a strict normal glycemic range. However, because the balance of glucose production and removal are unknown, and not considered in the simple measurement of blood glucose concentration, using blood glucose concentration as the diagnostic and insulin as the treatment often leads to wide swings in blood glucose concentration. Regrettably, despite diligent efforts on the part of clinicians attempting to maintain patients by dextrose drip and pushing insulin to normalize blood glucose concentration, the patient will be maintained at the perceived ideal blood glucose concentration range for only short periods of time. Additionally, the risk of hypoglycemia from too aggressive insulin therapy is also a serious risk and increased with intensive insulin therapy. Recognizing the difficulty of using dextrose and insulin therapy to maintain blood glucose concentration in injured and ill patients others have created computer-assisted record keeping devices to assist in therapy (59), while others have studied the benefits and liabilities of early versus late parenteral complement to enteral and oral nutritional support to achieve better patient outcomes and shorter hospitalization times (18). The methods fail for lack or knowing the underlying mechanisms of flux (metabolite appearance and disposal).

A better understanding of the pathophysiology resulting from the stress of critical illness is desired and, in fact, needed to better care for patients. Now, by means of our invention, using fractional GNG measurements a clinician shall be able to determine the exact nutritional and metabolic state of the patient, and therefore, be able to effectively intervene in illnesses such as, but not limited to, preterm infant care, complications from pregnancy requiring hospitalization, pre-operative surgery preparation and post-surgery monitoring, stroke, aneurysm, terminal illness, urinary sepsis, cardiac failure (post-cardiac surgery), esophagectomy for carcinoma, subarachnoid hemorrhage, ileus, subdural hematoma, pulmonary sepsis, cardiac failure (post-myocardial infarction), respiratory failure (chronic obstructive pulmonary disease), oropharyngeal abscess, coronary bypass, resection of thoracic aneurysm, starvation, burns, severe acute respiratory syndrome ("SARS") and potential epidemics and pandemics relating to influenza can be treated more precisely according to the individual nutritional needs based on the patients energy demands from their individual metabolic state.

The term "patient" often refers to an individual (human, other mammal or even other animals) suffering from injury or chronic disease. It can also refer to acutely or chronically stressed individuals such as premature infants, the chronically malnourished, underfed and physically exhausted athletes, soldiers and manual laborers, subjects in studies of pharmaceutical development, and many others. It can and here is intended to apply to individuals who also do not fit obvious or conventional notions of injured or ill patients, but can benefit from diagnostic, feeding or other treatments.

In fact, fractional GNG has already been measured in persons suffering many of the illnesses listed above; however, to date none have recognized that the nutritional needs of ill and injured patients could be met by targeting a constant range. The inventors, among others, have observed that a 12-hour fasts results in a fractional GNG of about 40%, while starvation over several days will drive fractional GNG above 90%. According to the invention, treatment of an ill or injured individual would involve negative feedback control of enteral nutrition and MCC infusion: response to high % GNG would be increasing enteral nutrition and MCC infusion, whereas low % GNG would mean over nutrition and the need to reduce feeding rate. A range of near 25% is generally an appropriately fed state, 3-4 hr after a balanced, CHO-containing meal. In healthy, uninjured individuals, a low level of fractional GNG, around 10% would be measured soon after they consumed a balanced, CHO-containing meal. A low fractional GNG of around 10% in a comatose individual, such as a TBI patient in an ICU, a GNG of 10% is unlikely, as has been observed by the inventors and other researchers, in studies to be published in the coming months, but would be indicative of over feeding and the need to reduce enteral feeding and MCC infusion until % GNG is in the 20-25% range, thus avoiding some of the consequences as described above. More typical of a TBI patient in the ICU would be % GNG >40%, thus requiring increased provision of enteral nutrition and vascular MCC infusion. In the case of a brain-injured person, the approach should be to maintain glycemia with both enteral nutrition and MCC infusion, the latter being important to supply cerebral nutrition and electrolytes to reduce cerebral swelling and minimizing hyperglycemia from dextrose.

In one embodiment, fractional GNG of 20-25% is aimed for, in another 15-35%. Regrettably, none of the current art has recognized that fractional GNG is the key biomarker of the pathophysiology related to critical illness. Regrettably also, none have used knowledge of fractional GNG to assess patient nutrient needs. We have devised such methods for intravenous, oral or gastric nutrient delivery to patients.

Large and extensive studies have been conducted to understand the benefits associated with nutritional support (18). Such studies have gone to some lengths to understand the patient's nutritional needs, but they have not found a good biomarker to indicate if patients are well nourished, overfed or underfed. Without the underlying metabolic state of the patient it is impossible to know what the exact nutritional needs are of that patient. Therefore, despite studying over 5000 patients, the above study was unable to determine a clear advantage to early parenteral nutrition to complete the enteral nutrition. They did, however identify negative consequences from overfeeding and underfeeding, but it is not clear that they are able to ascertain the precise nutritional status of their patents.

Some studies (65) have used indirect calorimetry in order to determine the exact energy expenditure over a 24 hr period and then administer 100% of the nutrients required to meet the energy expenditure of the individual patient. However, a close evaluation of their data reveals the percent contribution of glucose from gluconeogenesis indicates their patients were overfed. Despite the attempt to measure energy expenditure and deliver 100% of needed nutrients enterally, they inadvertently overfed their patients. Overfeeding like underfeeding, of hospitalized patients can result in serious negative consequences including infection, prolonged ventilation, metabolic disturbances (hyperglycemia, dyslipidemia, liver dysfunction), morbidity and mortality (50).

Some Other Applications

Already described are patient treatments following trauma and chronic illness. The invention also includes methods for managing those extreme and other cases and instances when assessment of BES, diagnosis and treatment are appropriate. Such examples include, but are not limited to assessing BES of patients or others before and after surgery, before and after drug treatment or dietary intervention, or any situation in which knowing, or standardizing BES is essential for determining outcome of any treatment, or establishing the effect of said treatment on humans or other mammals.

An example of using the new invention to set the BES background in which to evaluate safety, efficacy and functionality in the process of drug development. Drug development is a term used to describe the process of bringing a drug to market that includes pre-clinical research including animal studies, and human clinical trials, potentially leading to regulatory approval. In well-fed individuals % GNG can be as low as 10%, whereas after several days in the ICU % GNG could be 70% in TBI patients. Given this 7-fold range in GNG flux, pharmaceutical manufacturers with drugs that can affect metabolic flux rates several-fold would have a difficult time demonstrating effectiveness of their new drug. Therefore, with the present invention of being able to determine, and nourish individuals to the point of controlling GNG and establishing a stable background in which to evaluate effectiveness of a new drug, the patient treatments could be optimized. Also, costs associated with testing for the effectiveness of new drugs could be minimized.

Additionally, the application of % GNG may also improve dose response and efficacy for already established drugs or for new uses for drugs already on the market. For example, the commonly used drug Decadron (Dexamethasone) may have a new application in post-surgery applications for inflammation. However, it is anticipated that Decadron will affect the metabolic function of the patient. This augmented metabolic function might cause the patient to become catabolic simply from the administration of the drug and thus obviate the desired anti-inflammation characteristics of the drug by causing an undesirable side effect. If this action were to happen, the application for the drug might be interpreted to cause the patient to have a poor outcome. However, the outcome might be enhanced by proper nourishment using % GNG as a diagnostic. Under an appropriately nourished state, the administration of Decadron could minimize inflammation, leading to desired affect of administration of the drug and potentially a better overall outcome for the patient.

Determination of % GNG and The Timing, Type and Amount of Nutrient Delivery

Fractional gluconeogenesis (% GNG) will typically be determined on patients in the morning so that the Part 1 measurement can be made, interpreted in Part 2, and the target GNG or % GNG achieved during the work day. By this schedule, it can be anticipated that GNG be determined 3 times during the day, ideally morning, noon and evening. The morning measurement will provide important information on the patient's nutritional state through the evening and effectiveness on the ongoing, individual patient's needs for enteral nutrition and MCC infusion to achieve % GNG in the target range. Importantly, also, the morning measurement will inform clinicians to the need to adjust rates of enteral nutrition and MCC infusion. The noon, or early afternoon measurement will be important to monitor the individual patient's changing state, and to evaluate effectiveness of morning adjustments to achieve the target % GNG. And, the evening measurement will be important to establish stability of blood glucose concentration and % GNG in the patient during night hours when medical attention is typically less frequent.

Recovery from Illness and Trauma and Resumption of Oral Feeding

With the above described treatments (A-D) exquisite glycemic control shall be accomplished in comatose patients. However, procedures need to be in place for when patients recover consciousness sufficiently to allow the taking of some oral, including real-food, nutrition, but continue to require intravascular nutrient support. In all conditions, whether determined on patients after arising in the morning, or after a 12-hr fast, the target % GNG of 25% remains in place. For example, because most dietary energy might be consumed during awake hours, parenteral nutrition may be insufficient to prevent GNG from exceeding 25% of glucose Ra. Accordingly, food and parenteral nutrition would be given to achieve the target range of ~20-25% GNG.

Care of Infants

The exhaustive body of literature cited above deals largely with the care of injured and ill adults. However, the CDC reports 500,000 pre-term births annually in the US. Pre-term is the birth of an infant prior to 37 weeks of gestation. Pre-term birth is the most frequent cause of infant death, and leading cause of neurological disabilities (49). Such children are in obvious need of nutritive support, whether or not surgery is required for survival, and the provision of nutritive support may avoid the development of conditions such as cerebral palsy, developmental delay, hearing impairment and other neurological disabilities and death. Although not highly developed in the literature, the provision of nutritive support to premature infants, and the monitoring of gluconeogenesis have been subjects of investigation (43, 77). Gluconeogenesis has been reported to be established 4-6 hr after birth in full-term children (43), and gluconeogenesis does respond to the availability nutritive support (77). Extremely low birth weight pre-term infants do present abnormalities in the ability to regulate GNG in response to nutrient supply (19), but nutritive support is none-the-less essential to the survival in such infants.

Care of Ill or Injured Mammals

Significant portions of the invention, principles, theory and practice would likely apply to the care of most mammals (11, 23) and others (37, 72, 84). A notable exception will apply to the care of ruminant mammals whose gut is evolved to digest fibrous plant materials such as cellulose to propionate (42), which is closely related to lactate (2-hydroxy-propionate). Hence, in the case of ruminant mammals, the nutritional formulation could include 0-100% propionate.

Nutritive Formulations

Nutritive formulations to be given to patients after estimation of GNG (and in some cases, other biomarkers as well), has been discussed above, but will be discussed in more detail below.

Lactate-Based Formulations (Sanguisal-L)

In its simplest form, the MCC cocktail would be sodium-L-(+)-Lactate prepared by titrating L-(+)-Lactic acid with NaOH. The following describe such procedures:(24, 52, 55-57). Briefly, the MCC infusion cocktail is prepared by mixing concentrated (30-88%) L-(+)-lactic acid solution (e.g., Sigma-Aldrich or PCCA) in 2 N NaOH to pH 4.8, In the example provided, the starting point is a 30% stock lactic acid solution: 300 g 30% lactic acid stock solution is titrated with 133.3 g 2N NaOH and diluted to 1,000 ml with water. This will produce a 11.2% weight-by-volume ("w/v") MCC cocktail (sodium-L-(+)-Lactate) with an osmolality approximating 2,000 mOsm/l. Depending on the stock lactic acid solution used, a NaOH titrating solution >2 N may be necessary to neutralize stock lactic acid without exceeding the intended volume. Regardless of the specifics of acid titration, a 1.72% $Na^+$-lactate aqueous solution is isosmotic (308 mOsm/l); consequently, as initially mixed the above described MCC is far too concentrated to be given in a peripheral vein and will need to be diluted to less than 1,000 mOsm/l (a 5.6% $Na^+$-lactate solution). In a peripheral arm vein and a 5.0-5.6% $Na^+$-lactate MCC should be given with normal (0.9%, 308 mOsm/l) saline or another isosmotic solution such as 5 mM glucose (dextrose) in water, commonly called D5W (see more below).

This isosmotic admixture of MCC and diluent at the MCC infusion site will be sufficient to maintain vessel patency and prevent phlebitis or hemolysis at the infusion site (56). In a large vessel a 5% $Na^+$-lactate MCC cocktail could be given without expectation of hemolysis at the infusion site (57). Regardless of the dilution, the initial MCC solution delivery rate should be adjusted to deliver 10-50 (micro Moles) µMoles/kg/min, with maintenance infusion rate targeting blood lactate concentration of 3.5-4.5 mM, although higher levels (6 mM) have been used without ill effects (57, 71). Consistent with section methods described above, an infusion rate of 11 µMoles/kg/min would deliver the mass equivalent of 1.0 mg/kg/min of glucose, and infusion rate of 23 µMoles/kg/min of sodium lactate MCC would deliver the mass equivalent of 3 mg/kg/min glucose, and an infusion rate of 50 µMoles/kg/min would deliver the mass equivalent of 4.5 mg/kg/min of glucose. Ideally, the MCC is prepared from highest purity materials, is pathogen free, certified for human pharmaceutical use and is delivered into a large central vein, but peripheral vein can be used if administered with physiological saline to minimize osmolality and pH effects at the infusion site that might provoke phlebitis of hemolysis.

In another version of the simplest form, the MCC cocktail would be sodium-L-(+)-Lactate prepared from the dry, powdered salt in deionized water to the concentration intended [e.g., for an isosmotic solution: 154 mM lactate (plus 154 mM $Na^+$) total osmolarity 308 mOsm/l], and infused in the above-stated amounts to raise arterial [lactate] to the intended levels.

In the preferred form of the simplest iteration, the basic sodium-L-(+)-Lactate cocktail would be amended to include other lactate salts as exist in the plasma of healthy humans. Sodium ion ($Na^+$) is the main cation in plasma, normally 145 mM, and values for $K^+$, $Ca^{++}$, and $Mg^{++}$ are, respectively, 4, 2.5 and 1.5 mM. Hence, a mixture of inorganic lactate salts comprised of $Na^+$-, $K^+$-, $Ca^{++}$-, and $Mg^{++}$-lactate would be combined in the ratio of 144, 4, 2.5, and 1.5, In this embodiment of invention, the main anion would be lactate, but phosphates are important ions in energy metabolism and would be added in the form of 1 mM $NaH_2PO_4^-$. Because $Na^+$, $K^+$, $Ca^{++}$, $Mg^{++}$, and $H_2PO_4^-$ are present in the plasma of healthy individuals at levels of 145, 4, 2.5, 1.5, and 1.0 milliequivalent per liter (mEq/l) (53). This particular embodiment of MCC could be termed "Sanguisal" from the Latin words for blood (sanguis) and salt. To reiterate from above, the provision of sodium and other cations as a means to deliver lactate anions in an MCC has the advantage of reducing brain swelling following TBI (15) as well as providing nutritive support to intensive care patients following trauma (70).

Pyruvate-Based Formulations (Sanguisal-P)

As an alternative to Sanguisal-L that uses lactate as the major anion (vide supra), Sanguisal-P will involve the use of pyruvate (P) as the major anion, while at the same time maintaining the above-stated levels of cations {$Na^+$, $K^+$, $Ca^{++}$, $Mg^{++}$, and $H_2PO_4^-$ as are present in the plasma of healthy individuals: 145, 4, 2.5, 1.5, and 1.0 mEq/l}. Like its counterpart lactate, pyruvate is the precursor to lactate in glycolysis. Further, pyruvate is an oxidizable fuel and GNG precursor whose metabolism may affect cell redox status if converted to lactate. Further, pyruvate possesses antioxidant properties (48). Although typically present in 1/10 or lesser concentration compared to lactate, pyruvate has been introduced into the systemic circulation of large mammals in which the circulation has been interrupted to mimic cardiac arrest (61-63, 68). In such cases 100% pyruvate infusion raises the circulating pyruvate level, but more so, the circulating lactate level achieving a circulating L/P of 2-3, None the less, because of its chemical structure, pyruvate has the advantage over lactate of serving as an antioxidant in the myocardium subjected to reperfusion injury, and, by extension exogenous pyruvate my also serve to scavenge free radicals in the brain after blood flow is interrupted. A problem with regard to the use of Sanguisal-P, in contrast to the Sanguisal-L form, is that in circulation pyruvate is rapidly converted to lactate due to the effects of lactate dehydrogenase in red blood cells and the lung parenchyma (41). Hence, for the antioxidant properties of pyruvate, the optimal site of Sanguisal-P infusion would be in the carotid artery or ascending aorta. Still, by the ability to infuse mixtures of Sanguisal-L and Sanguisal-P into the systemic circulation, ascending or carotid artery, the clinician would have the opportunity to affect redox status in an injured brain. However, because carotid or ascending catheterization is uncommon even in the ICU, systemic solutions of a very low L/P ratio (i.e., high P/L) such as infusion of 100% Sanguisal-P, or a mixture of Sanguisal-P/Sanguisal-L of 2.0 (L/P=1/2 in the infusate), would serve to raise the arterial level of pyruvate relative to that of lactate.

In its simplest form, Sanguisal-P would be sodium-L-(+)-Pyruvate prepared by titrating L-(+)-Pyruvic acid with NaOH as described above for lactate (24, 52, 55-57). As with lactate (vide supra), the initial $Na^+$-pyruvate infusion rate would deliver 11-50 (micro Moles) µMoles/kg/min, with maintenance infusion rate targeting blood lactate concentration of 3.5-4.5 mM, although higher levels (6 mM) have been used without ill effects (57, 71). Consistent with section methods described above, infusion rate of 11 µMoles/kg/min of sodium pyruvate MCC would deliver the mass equivalent of 1.0 mg/kg/min of glucose, an infusion rate of 23 µMoles/kg/min would deliver the mass equivalent of 3 mg/kg/min glucose, whereas an infusion rate of 50 µMoles/kg/min of sodium pyruvate MCC would deliver the mass equivalent of 4.5 mg/kg/min of glucose. Ideally, the $Na^+$-pyruvate MCC is prepared from highest purity materials, is pathogen free, certified for human pharmaceutical use and is delivered into a large central vein, but peripheral vein can be used if administered with physiological saline to minimize osmolality and pH effects at the infusion site that might provoke phlebitis of hemolysis.

In another version of the simplest form, the MCC cocktail would be sodium-L-(+)-Pyruvate prepared from the dry, powdered salt in deionized water to the concentration intended, and infused in the above-stated amounts to raise arterial [lactate] to the intended levels. To reiterate, manufacturing and storing pyruvate-containing formulations such as Sanguisal P and Sanguisal L-P mixtures should be anhydrous. Pure sterile water can be added immediately before delivery to avoid pyruvate degradation and accumulation of undesired pyruvate degradation products.

In the preferred form of the simplest iteration, the basic sodium-L-(+)-Pyruvate cocktail would be amended to include other pyruvate salts as exist in the plasma of healthy humans. Sodium ion ($Na^+$) is the main cation in plasma, normally 145 mM, and values for $K^+$, $Ca^{++}$, and $Mg^{++}$ are, respectively, 4, 2.5 and 1.5 mM. Hence, a mixture of inorganic lactate salts comprised of $Na^+$-, $K^+$-, $Ca^{++}$-, and $Mg^{++}$-lactate would be combined in the ratio of 144, 4, 2.5, and 1.5, In this embodiment of invention, the main anion would be pyruvate, but phosphates are important ions in energy metabolism and could be added in the form of 1 mM $NaH_2PO_4^-$. Because $Na^+$, $K^+$, $Ca^{++}$, $Mg^{++}$, and $H_2PO_4^-$ are present in the plasma of healthy individuals at levels of 145, 4, 2.5, 1.5, and 1.0 milliequivalent per liter (mEq/l, this particular embodiment of MCC could be termed "Sanguisal" from the Latin words for blood (sanguis) and salt (53); in this case Sanguisal-P (for pyruvate). To reiterate from above, the provision of pyruvate and other cations as a means to deliver lactate anions in an MCC has the advantage of reducing brain swelling following TBI, as has been observed by the inventors and other researchers in studies to be published in the coming months, see also (15). The invention can also provides nutritive support to intensive care unit patients following trauma (70), and acting as a reactive oxygen species ("ROS") scavenger (48).

In this preferred form, Sanguisal-P would be prepared from the dry, powdered pyruvate salts ($Na^+$, $K^+$, $Ca^{++}$, $Mg^{++}$, and $H_2PO_4^-$) in the ratios of 145:4:2.5:1.5:1.0 in sterile deionized water to an anion concentration of 154 milliequivalent per liter (mEq/l), and infused in the above-stated amounts to raise arterial [pyruvate] to 1-2 mM and an arterial [lactate] in the intended range.

Lactate and Pyruvate Combination-Based Formulations (Sanguisal-L/P)

Isosmotic (154 mM) mixtures of Sanguisal-L and -P may be mixed and used to change the circulating L/P. Infusions of 2N $Na^+$-Pyruvate into swine were observed to raise arterial [pyruvate] to 3.5 mM and [lactate] to 8 mM for an L/P in the range of 2-3 (68). If an arterial L/P of 10-11 is typical of healthy resting humans (36), then infusing a Sanguisal mix of 2 parts Sanguisal-P to 1 Part Sanguisal-L may reduce an elevated systemic L/P to that seen in healthy individuals. Then, by observation, the clinician has the ability to lower the circulating L/P by lowering the L/P of the Sanguisal mix given. Conversely, the clinician has the ability to raise the circulating L/P by increasing the L/P of the Sanguisal mix given. In summary, Sanguisal (S) mixes of 100% S-Pyruvate to 100% S-Lactate may be used to provide nutritive support to the injured brain and other injured or non-injured tissues, provide a gluconeogenic precursor, and scavenge ROS in all tissues perfused.

With regard to the infusion of Sanguisal-P, one may logically ask: "why is the resulting arterial [lactate] monitored?" There are practical as well as scientific reasons for this. From the practical standpoint, rapid lactate, but not pyruvate analyzers are available. And scientifically, lactate is the preferred monocarboxylate compound (MCC) in nature: the L/P in arterial blood of healthy individuals is minimally 10, and rises more than an order of magnitude in normal physiology. Secondly, pyruvate is rapidly converted to lactate in the blood by the action of lactic dehydrogenase in erythrocytes (RBCs) in the blood (69) and the lung parenchyma (41), and lactate, not pyruvate, it the major fuel source and GNG precursor (see above).

Regardless of whether Sanguisal-L, -P or -L/-P mixtures are administered, the clinician will monitor % GNG and titrate the Sanguisal infusion rate with the target to achieving approximate estimates of GNG between 15-30%.

Lactate Esters as MCCs

As described herein, Sanguisal-L and -P are inorganic salt-based means to deliver nutritive support. However, it is possible to deliver lactate and other nutritive compounds (pyruvate and acetate) by other means, including esters. Arginyl lactate (U.S. Pat. No. 5,420,107) has been extensively used as an (enteral) amendment to sports drinks to provide energy and blood buffering (1, 25). Arginyl lactate is formed by the electrostatic binding of lactate from lactic acid and the basic (zwitterion) amino acid arginine under basic conditions. These individual units dissociate spontaneously at neutral pH as exists in human plasma. The components of arginyl lactate (arginine and lactate) are benign and efficacious in human blood.

Similarly, the lactate thiolester formed from the combination of lactate and N-acetylcysteine (called "LNACE", see, for example, U.S. Pat. No. 6,482,853) has been proposed as an amendment to sports drinks to provide energy and blood buffering. Like arginyl lactate, LNACE is yet another platform for parenteral nutrition of an ill or injured patient.

Still another means to deliver parenteral nutrition of an ill or injured patient is glycerol tri-lactate (called "GTL", see, for example, U.S. Pat. No. 6,743,821). Glycerol tri-lactate is formed by the esterification of glycerol by lactic acid by means of organic or enzymatically catalyzed processes (see, for example, U.S. Pat. No. 6,743,821). These individual units rapidly dissociate because of the lipases and esterases in human plasma. The components of GTL (glycerol and lactate) are benign and efficacious in human blood. Glycerol has been used as a plasma expander (76) and gluconeogenic precursor (73). In terms of nutrient delivery, GTL is preferred over sodium- and other inorganic salts of lactate because more lactate is carried, no sodium load is incurred, and because the glycerol carrier is efficacious.

Still another means to deliver parenteral nutrition of an ill or injured patient is glycerol tri-acetate (called "GTA", see, for example, U.S. Pat. No. 6,743,821), or acetin. Acetate is another body, although not brain, fuel energy source.

Lactate, Pyruvate and Dextrose Combination-Based Formulations (Sanguisal-L/P/D)

State of the art is to provide parenteral nutritive support to patients using 5% dextrose (D5W, glucose in water, vide supra). Because glucose (dextrose) has a molecular weight of 180, osmolality of D5W is 278 mM, which in the low range of normal plasma osmolality (275-310 mEq/l). Even though the glucose concentration in D5W is 50 times greater than homeostatic in plasma, in terms of its isosmotic effect with glucose alone being the only solute, D5W is isosmotic. Mixing equal isosmotic solutions such as equal volumes of 154 mM Sanguisal-L and D5W glucose will produce an osmolality in the high end of the normal range. As noted earlier, this slightly elevated osmolality because of sodium content will draw fluid from tissues into the vascular compartment, thus mitigating swelling due to injury (15).

Lactate, Pyruvate, and Amino Acid Combination-Based Formulations (Sanguisal-L/P/A)

Parenteral nutrition is provided to hasten nutrient delivery or gastro-intestinal and other conditions exist to limit the enteral delivery of nutrients. The above-identified Sanguisal formulations are all carbohydrate (CHO)-based and can be used and adjusted to nourish the injured brain and other organs. In vivo, energy balance and nitrogen balance interact, the RDA for amino acid and protein intake being 0.8 g/kg body weight/day (8, 51), with the assumption being that the diet supplies sufficient energy to maintain energy balance. Although the latter assumption is seldom recognized with athletes taking upwards of 2 g/lb/body weight (60), even very high protein diets that are accompanied by a very high nitrogen load, will lack energy to maintain a person in nitrogen balance. Accordingly, in attempts to maintain nitrogen balance and body mass in injured and ill patients, amino acid and protein supplementation to the extent of 50% above the RDA for amino acids and proteins on the background of adequate energy supply is deemed prudent (82).

Commercially available parenteral amino acid solutions contain essential and non-essential amino acids. In contemporary literature, investigators have evaluated effects of emphasizing particular amino acids, and types of amino acids including: glutamine, arginine, cysteine, taurine, and branched chain amino acids ("BCAA", leucine, isoleucine, and valine, particularly leucine). At present it is clear that parenteral solutions containing mixes of essential and non-essential amino acids are safe and efficacious, being part of routine parenteral nutrition. Such solutions are typically hyperosmotic, but less than 1,000 mOsm/l. As such, current art allows that infusions of Sanguisal-L, Sanguisal-P, or mixes of Sanguisal (L/P), could be augmented by infusions of amino acid parenteral solutions delivering 1.0-1.2 g nitrogen/kg body weight/day.

Lactate, Pyruvate, Dextrose and Amino Acid Combination-Based Formulations (Sanguisal-L/P/D/A)

When % GNG is unknown, with the assumption that blood glucose can be monitored in real time, a clinician can provide parenteral and enteral nutrition as described above. In the event of hepatic or renal failure, and consequent limitations in a patient's ability to clear sodium or regulate glycemia by means of providing GNG precursors, a clinician may moderate the course of providing lactate- and, or, pyruvate-based MCCs, and instead supplement the patient with D5W, in extreme hypoglycemia, D10W (5 mM glucose (dextrose)).

Adding $D_2O$ to Sanguisal Formulations

For assessment of GNG using the $D_2O$ method, first responders will need to take a first ("background") blood sample before the injection of $D_2O$. As noted above, the 0.3 to 0.5% $D_2O$ abundance necessary to estimate GNG from the penta-acetate derivative of glucose and GC/MS could be obtained by a bolus of $D_2O$. However, also as noted above, the 0.3 to 0.5% abundance of $D_2O$ could be maintained over days and weeks by adding $D_2O$ to all infusates given to TBI and other injured and ill patients. As Sanguisal solutions will be given to provide parenteral nutrition and maintain glycemia, as a preferred form, $D_2O$ could be to make Sanguisal solutions 0.3 to 0.5% $D_2O$. Another preferred form of $D_2O$ could be to make common intravenous saline solutions 0.3 to 0.5% $D_2O$ as the majority of the exogenous fluids delivered to an ill or injured patient comes form the intravenous ("i.v.") saline solutions routinely used in the hospital. If the exogenous fluid load can be controlled by the clinician through use of the common i.v. saline solution, then the enrichment of body water by deuterium can also be controlled and therefore the measurement of % GNG can be made for the duration of the stay at the hospital as frequently as required by the attending clinician. For example, if 100% of the exogenous solution come from the i.v. saline solution and the i.v. solution is a 1 liter bag, the i.v. solution will have approximately 0.3 to 0.5 g of $D_2O$ added. If enteral feeding, for example, contributes 25% of the exogenous fluids, then the $D_2O$ saline solution could contain 25% more $D_2O$ to accommodate for the increased ingestion of exogenous fluids. Therefore the saline solution would now contain approximately 0.375 to 0.625 g $D_2O$.

Nutritional Support and Lactate Range Targets Without, or In Advance of, BES/% GNG Measurements Assessments of the BES % GNG of the patient by % GNG may not be immediately available and in some cases may not be feasible for hours, or days following an injury or illness incident. In addition, follow-on metabolic crises provoked can develop quickly, before measurements can be made. Therefore, the invention also provides for effective ways of feeding and treating a patient in the absence of such BES measurements.

The general approach of this embodiment of the invention is to target a range or ranges of blood lactate concentrations, [lactate] using formulations containing sodium-lactate, lactate esters and polymers, and/or other MCC and GNG precursors. This helps ensure adequate energy supply and limited catabolism of the patient far better than simply targeting a [glucose] range as is done in the current art.

The [lactate] can be measured as easily as [glucose] can be (in a drop of blood), and so can be taken such at the site of an incident such as a sports venue, battlefield, emergency vehicle, as well as hospital emergency room or ICU. To reiterate and expand upon what has been stated above, because blood glucose homeostasis is such an important physiological priority, and because redundant physiological mechanisms are in place to maintain blood glucose concentration, [glucose] provides no information on the BES of a patient unless it falls well outside of normal physiological range. At this point, dire hypoglycemia or hyperglycemia conditions exist for the patient. More importantly, in this aspect of the invention, [glucose] measurements also do not provide actionable data on what nutritional action to take— by contrast, [lactate] does provide such actionable data, even if it does not provide true insight into the BES of a patient.

Of the GNG precursors, lactate is by far most important (11, 12, 24, 54, 113). As part of the body's protective fight-and-flight mechanism, blood lactate generally rises, and this rise acts to provide lactate as a GNG precursor and fuel for injured and other tissues. However, depending on the manner and time of injury and the nutritional state of the patient, the rise in lactate may be inadequate to meet patient needs especially as the body energy stores are depleted.

Lactate (24, 52, 55-57, 104) and other MCC or GNG precursor supplementation are of great benefit to the patient not only because it is a fuel energy source for the body in general (3, 5-7, 55, 56, 104, 112, 116, 117), but because it is especially important for tissues and organs such as the brain (33, 105, 115, 118). In addition, it is known that the brain swelling that accompanies injury can be mitigated by providing sodium ions using lactate as the carrier vehicle (108).

Lactate supplementation, whether given orally or intravenously, is known to provide fuel to the working muscles of athletes and others engaged in vigorous physical activity. Oral or intravenous administration of lactate is safe and has no apparent side effects except mild alkalosis. This can possibly being an actual advantage to the ill or injured when acidosis is a problem (101) as it is in high-intensity exercise and hypermetabolic patients.

As stated above, the invention provides for various methods and systems for assessing BES and providing nutritive support. The interim between onset of injury or sudden illness and the assessment of BES by % GNG can be a period of nutritionally unsupported risk to the patient without immediate supplementation. The benefits of lactate supplementation to athletes are here adapted for use with ill, injured and nutritionally compromised patients. Hence the inventors now describe targeting a range of [lactate] concentration as both an interim and even long-term method for providing for the nutritional needs of the patient. Infusion of lactate or other MCC or GNG precursor can also be provided even before measurement of [lactate], to be on the safe side in terms of providing adequate nutrition to the patient.

Note also that [glucose] is generally not affected by supplementation by lactate or other MCC or GNG precursors because of the preferential use of lactate as a fuel energy source and autoregulation of hepatic glucose production ("HGP"). Because HGP is tightly controlled, elevated availability of GNG precursors (such as the MCC, lactate) will increase the component of HGP from GNG, and decrease the contribution of GLY. Thus [glucose] is not only generally less useful than [lactate] as a indication of nutritional needs, it is especially limited with respect to the nutritional protocols of the current invention.

The liver uses exogenous as well as endogenous reserves of lactate, pyruvate, glycerol, alanine and other gluconeogenic amino acids to produce glucose via GNG. This catabolism of body tissues to support GNG has both short- and long-term negative consequences including body wasting. Providing lactate or other MCC or GNG precursors (that quickly become lactate) to an ill or injured patient will mitigate catabolism of body tissues. As noted above, a normal [glucose] may belie metabolic stresses within a body working very hard to maintain glycemia in the normal range and thus is depleting body energy stores and tissues.

The biomarker blood [lactate] is well known in the art and simple to assess from a blood test used to determine the level of metabolic stress in athletes and others engaged in vigorous physical exercise. Recent papers show that in contrast to classical thinking, providing lactate orally or intravenously can enhance an athlete's physiological status and performance. Intravenously provided lactate supports blood glucose homeostasis in at least two major, related ways. Lactate is a GNG precursor and lactate is itself a major fuel source (4, 104, 112, 116, 117) surpassing glucose in magnitude of both concentration range and metabolic flux rate of use/production).

In fact, providing exogenous lactate in effect spares the blood's circulating glucose from metabolism because lactate is the preferred energy source. This leaves the meager glucose reserves of the blood (5 liters of blood, each containing 1 gram of glucose with only a total caloric value of only about 20 kcal-oxidation of each gram of glucose yields 4 kcal) available to the body.

As an analogue to the BES of an ill or injured person, we can use the example of a resting 12-hr overnight fasted healthy male. This fasted person will use approximately 1.8 kcal/min of total energy, with carbohydrate (CHO: glycogen, glucose and lactate) providing about 40% of the energy, lipids about 50%, and proteins and amino acids the remainder, about 10% (103). In this context, in contrast to providing i.v. glucose, providing lactate or other MCC or GNG precursors can make up for the CHO and energy deficits. Because of the autoregulation of hepatic and renal autoregulation of blood [glucose], this approach of providing GNG precursors will provide glucose at moderate but sustained rates and will not provoke a spike in blood [glucose] that will elicit a strong insulin response. Avoidance of this hyperinsulinemic insulin response is desirable, because it often results in a metabolic roller coaster wherein the patient is given glucose, which drives [glucose] very high, thus invoking an insulin response, which drives [glucose] very low, followed by another cycle of i.v. glucose and insulin injections and infusions (vide supra).

If we provide nutritional supplementation to a patient as described below, we will allow the patient to be functionally hypermetabolic, that is using energy at a high rate but also being fed energy at a high rate. This will cause the patient to have a BES similar to that of an athlete doing mild to moderate intensity physical exercise, where both the relative use of CHO-derived energy sources and total energy expenditure (kcal/min) are elevated.

Note that a lactate clamp (LC) is a glucose clamp, in that a particular [lactate[ or range is targeted, as is done in the art with [glucose] and glucose. In the invention, we implement a lactate clamp with an infusion of a sodium lactate or other MCC or GNG precursor cocktail that raises blood [lactate] to 4 mM, or other target blood [lactate] or range. As described in the invention, infusion of sodium lactate or other MCC or GNG precursor cocktail is followed by frequent monitoring of blood [lactate], with increases or decreases in infusion rate as the target blood [lactate] is achieved and maintained. Note that when a LC is employed in exercising healthy young men (where the total energy expenditure can be greater than 10 times that at rest) exogenous and endogenous lactate make up the majority of CHO-energy used by the body at that time (104).

Although the hypermetabolic patient as described will generally resemble an exercising human more than a resting person, the examples provided with the invention describe a range of responses. Lactate, including vascularly supplied exogenous lactate, can play an important role as a body energy source in all of them. The [lactate] level at which the beneficial effects of exogenously supplied lactate occur is above normal (1-2 mM), generally about 4 mM (102). Note that normal circulating [lactate] Hence, [lactate] is one target which indicates that sufficient lactate is on board to directly fuel an injured brain or other tissues, to indirectly fuel glucose-dependent tissues such as the brain via GNG, as well as to mitigate acidosis and tissue swelling (108).

The invention provides for estimating and targeting patient blood lactate concentration ([lactate]), both as a target itself and as an intermediate step to estimating and targeting patient fractional GNG in body glucose production. Nutritional support methods and formulations are also disclosed that can be used in conjunction with BES/% GNG estimate, as well as without these measurements.

The invention provides systems and methods to guide the administration of lactate or other MCC or other GNG precursor formulations to an injured or critically ill patient. The method can be used in either of two ways: (1) as a first step during the interim between the adverse patient illness or injury event and assessment of BES via % GNG. In a preferred embodiment, the initial lactate/MCC/GNG precursor infusion rate is about 3-4.5 mg/kg/min, where kg is kg of patient body weight and 3 and 4.5 mg are the amounts of MCC or GNG precursor such as sodium lactate.

Alternatively, about 23-50 µMol/kg body weight/mM between the time of injury or acute illness until BES can be determined via % GNG. The formulation infusion rate can be adjusted up or down to target such [lactate] levels. This helps ensure that [lactate] levels are adequate to (a) directly fuel the brain and other tissues, (b) indirectly fuel tissues with obligatory glucose needs (glucose created via GNG), (c) mitigate tissue swelling by decreasing intracranial pressure, and (d) mitigate metabolic or respiratory acidosis by affecting hydrogen ion removal through lactate shuttling as well as by and providing a strong anion. Other standard clinical values such as blood pH, electrolyte, total dietary calories and glucose levels, can also be targeted in various aspects of the invention.

The invention provides a method for estimating the lactate or other MCC or GNG precursor infusion rate needed to provide patient needs between the time of injury and assessment for BES by determining fractional gluconeogenesis of a patient. The method commences with administering at a lactate or other MCC or GNG precursor infusion rate, as described above, taking a small venous or arterial blood sample from the patient, analyzing [lactate], and adjusting the infusion rate to maintain the target blood [lactate] over time. A small (20-100 µl) sample of arterial, venous, finger or earlobe blood is typically used to measure [lactate].

The invention provides for the analysis of blood [lactate] by means of a clinical blood gas analyzer or similar device that is used routinely to determine blood acid/base status in a clinical setting. The invention also provides for the analysis of blood [lactate] by means of an approved portable, hand-held or other device as used in laboratory, clinical or field assessments in resting individuals or athletes or others performing vigorous physical exercise. Such devices are readily available, inexpensive, and used by sports medicine practitioners, athletes and coaches as are portable heart rate monitors. Although generally not as accurate as FDA-approved and other clinical devices, hand-held portable lactate analyzers are accurate in the mM range and can be used to establish a target a LC value or range while ill or injured persons are transported to clinical facilities. New, more portable and more sophisticated apparatus for analyzing [lactate], as well other biomarkers on interest in the invention, are constantly being developed and are contemplated by the invention.

With regard to total body nutritional calculations such as from the Institute of Medicine and others, parental supplementation of the current can included in these calculations, or in a preferred embodiment, added to these numbers. Hypermetabolic states, such as exist with TBI, will require an even greater total daily calories that may not be able to be delivered adequately enterally.

The formulations of the invention may also include one or more salts, one or more of $Na^+$, $K^+$, $Ca^{++}$, $Mg^{++}$, and $H_2PO_4^-$, and have an osmolality of less than about 310 mOsm, where the MCCs or GNG precursors are lactate or pyruvate or both. In a preferred embodiment an alternative to the formulation of less than about 310 mOsm as described above a stock formulation with an osmolality≈3,000 mOsm can be used so long as it is diluted with sterile hypotonic or isosmotic solutions (distilled water, half normal or normal physiological, 154 mM saline, so that the solution entering the body has an osmolarity of less than of about 310 mOsm, and in some cases less than about 1,000 mOsm.

The formulation may be administered at a rate of about 10-50 micro moles per kg of body weight per minute (μMoles/kg/min), where kg is kg of patient body weight and 10-50 μMoles is the amount of lactate or other MCC or GNG in the formulation, administered and the infusion rate increased or decreased if the measured blood [lactate] differs from the target value or values.

Lactate was once thought to be a waste product of metabolism owing to oxygen insufficiency and a cause of muscle fatigue and soreness (107, 111). Today as part of lactate shuttle theory, lactate is viewed as an energy fuel source, a GNG precursor and a signaling molecule, in other words a lactormone (5, 106). Lactate is produced continuously under fully aerobic conditions and is an essential metabolic intermediate at the crossroads of the pathways of carbon metabolism (5-7). In the outdated concept lactate was a liability. In the contemporary view lactate is a metabolite of great utility and importance.

Blood lactate concentration or [lactate], is also called lactatemia. Hyperlactatemia refers to elevated blood [lactate], as generally considered greater than that of rest (about 1-2 mM). In exercise physiology and sports medicine science, hyperlactemia with a value of 4 mM is often referred to as the lactate threshold ("LT"), also know as the onset of blood lactate accumulation ("OBLA") (12, 52, 102).

The target blood [lactate] of 4 mM refers to hyperlactatemia induced by exogenous vascular infusion of the current invention. Such a target [lactate] provides sufficient lactate to provide fuel energy, material for gluconeogenesis, and anti-inflammatory and buffering capacity.

In 1963, an inspired track and field athlete, inventor GAB, inquired of his collegiate coach about why he was incapable of making the US Olympic team despite serious efforts to do so. The coach answered in the conventional wisdom at the time that he had an oxygen debt and too much lactic acid. Subsequently, when looking for a Ph.D. dissertation subject, and realizing that century-old explanations were not consistent with then contemporary knowledge of physiology and biochemistry, GAB set out to study and conduct definitive studies on the physiology and biochemistry of oxygen debt and lactic acidosis. Thus, his interest in sports science proved to be the starting point for a career in studying the science of metabolic regulation. The course of discovery involved studies of oxygen uptake kinetics during exercise and recovery, isotope tracer studies of metabolite flux rates in animals and humans, and the molecular biology of tissue adaption to exercise and other stresses.

In 1984, realizing the significance of lactate flux and its integration and significance in intermediary metabolism, inventor GAB invented the term lactate shuttle to describe the exchange and use of lactate as an energy source within, between and among cell compartments, cells, tissues and organs. Since the original articulation of discovery, intracellular and cell-cell lactate shuttles have been described in the literature (vide supra). As well, others scientists have recognized generality of the principle and have described lactate shuttles within the brain (33, 64, 115, 118).

Realizing the importance of lactate as a fuel energy source, in 2002 the inventors developed the lactate clamp technique for the study of energy substrate partitioning in resting and exercising humans (55). Since then, the effect of lactate clamp technique on blood acid-base balance and electrolyte content has been determined (57), and the technique has been used to interrogate meaning of the "lactate threshold" ("LT") in exercising humans (52, 104). In exercising humans, the LT occurs at a blood lactate concentration of about 4 mM, though that concentration varies among individuals and depends on the conditions of study (102). An elevated blood lactate concentration in exercising humans allows for the use of lactate as fuel energy source and GNG precursor (2-4, 5-7, 24, 104, 112).

Therefore, one aspect of the invention provides for infusion of a formula containing MCC or GNG precursor or both, with periodic blood sampling and measurement to achieve a blood [lactate] target soon after injury or onset of serious illness. This can be a first step segue to the provisioning of nutrition based on the either estimation of [lactate] or % GNG or both. The target [lactate] concentration of the invention is in some cases, above about 0.5 to 1 mM, 0.5 to 1 mM being the bottom of the normal range for [lactate]. In other embodiments, it is above about 2 mM, 2 mM being the top of the normal range for [lactate]. In other embodiments it is above about 4 mM, 4 mM being the hyperlactemia level where beneficial effects occur all the way to about 8 mM. In another embodiment it is this entire range of normal to quite high, about 0.5-8 mM.

For example, in the case of trauma, such as in severe TBI, treatment will start with a formulation of the invention at a rate of about 50 μMol/body weight/min (about 4.5 mg/kg/min). When it is possible, blood [lactate] will be sampled at regular intervals to achieve the target blood [lactate]. Subsequently, according to the invention, one may increase, decrease, or maintain the MCC or GNG precursor infusion rate to achieve a target blood [lactate] value or range.

Using such a target [lactate] range can be an interim target until BES assessment via % GNG estimation becomes available. It also works in the invention as a stand-alone since high levels of [lactate] are generally well tolerated by patients. Thus it makes sense to err on the high side of [lactate]. Infusion of MCC or GNG precursor certainly raises blood [lactate], but it generally does not affect blood [glucose] (24, 55, 56).

Stability of blood [glucose] during lactate clamp procedure is attributable to autoregulation of hepatic and renal glucose production. If there is demand for increased glucose production, increased GNG precursor supply can support that need. However, equally likely is that increased GNG precursor supply will result in decreased hepatic GLY and stabilized glucose production (glucose Ra), and even glycogen synthesis. As well, exogenous lactate may substitute for peripheral glucose use. Therefore, the infusion of a MCC or GNG precursor solution may have an indirect, but small effect on glucose Ra depending on several factors including: recent dietary history, hypo- or hypermetabolic state of the patient, and level of sodium lactate infusion.

A small reduction in blood glucose flux can occur when lactate is used in preference to glucose as a fuel, thus decreasing glucose Rd. Again, as a result of the autoregulation of hepatic ("HGP") and renal glucose production ("RGP"), peripheral substitution of lactate for glucose as an energy source will decrease the needs for hepatic glucose production (via GLY and GNG) and RGP (via GNG). The use of LC procedure has additional beneficial effects: exogenous lactate buffers blood pH (lowers $H^+$ and raises pH), without major effects on plasma electrolytes (57).

However, while a blood [lactate] of 4 mM is a reasonable target that is familiar to practitioners of sports medicine and science, in and of itself the blood [lactate] value provides no direct information on lactate kinetics such as rate of appearance (Ra), rate of disposal (Rd), rate of oxidation (Rox), metabolic clearance ("MCR"), and of course GNG (2-4, 11, 24, 52, 53, 104).

The lack of ability to ascertain blood lactate kinetics from concentration has to do with importance of lactate metabolic clearance rate which is lactate Rd/[lactate] (4, 53, 102, 116, 117). Nonetheless, by means of commencing with exogenous lactate to achieve a stable blood [lactate], the invention provides sufficient lactate to provide nutritive support directly to an injured brain and other tissues, both directly as lactate, as well as indirectly via GNG.

It is also possible that subsequent to the initiation of the normative sodium lactate or other MCC or GNG precursor infusion rate (3-4.5 mg/kg/min), the resulting blood [lactate] might be 2 mM. Presentation of a low (about <2 mM) blood [lactate] will be interpreted to represent the presence of a hypermetabolic state with increased demands for lactate as fuel and GNG precursor, and will typically lead to an increase in the infusion rate, according to a preferred embodiment of the invention.

Alternatively, if the resulting blood [lactate] exceeds 8 mM in the absence of other enteral or parenteral nutrition, or if alkalosis or disturbances in plasma electrolyte levels occur, in the invention we may decrease the normative lactate infusion rate knowing that lactate Rd is <the combination of endogenous and exogenous lactate Ra.

When % GNG data is available, and % GNG is titrated to the ranges as indicated above, then the method will have optimal information on patient BES, and the interim target level of 4 mM no longer carries great weight as a feedback parameter on BES. However, [lactate] may still provide useful guidance. For instance, in an embodiment of the invention, in some situations, a [lactate] of 1-2 mM instead of 4 mM may be utilized, because % GNG indicates that sufficient energy from other energy sources exist for the brain and other tissues.

Hence, depending on knowledge of BES as determined by % GNG, the target blood [lactate] range can be as low as 0.5-2 mM, whereas in the absence of % GNG information, a range of about 4 mM and in some embodiments up to about 8 mM is desirable.

In the absence of % GNG, the MCC or GNG precursor infusion rate of approximately 3 mg/kg/min may continue until periodic blood sampling indicates that blood [lactate] reaches 4 mM, at which time the infusion rate will be maintained or adjusted up or down to maintain blood [lactate] at that target level. When % GNG data become available, the combination of enteral and parenteral nutrition will be maintained or adjusted to achieve the target of 25% GNG at which time exogenous MCC or GNG precursor infusion rate can be adjusted to maintain arterial blood [lactate] in the range of 1-2 mM (vide supra).

Parenteral nutrition can eventually be diminished or curtailed when enteral nutritional delivery is adequate to normalize BES, but intravascular $Na^+$-L-(+)-Lactate infusion may be maintained or restarted if the patient's BES indicates a need to supplement enteral nutrition and achieve approximately 25% GNG. $Na^+$-L-(+)-Lactate may also be used to manage intracerebral pressure ("ICP"). The invention, in a preferred embodiment, shall commence intravascular infusion of $Na^+$-L-(+)-Lactate at the rate of 3 mg/kg/min. In the absence of data on % GNG, the MCC or alternate embodiment infusion rate of approximately 3 mg/kg/min will continue until periodic blood sampling indicates that blood [lactate] reaches 4 mM, at which time the infusion rate will be maintained or adjusted up or down to maintain blood [lactate] at the target level.

When % GNG data become available, the combination of enteral and parenteral nutrition will be maintained or adjusted to achieve the target of 20-25% GNG in some embodiments, and 15-35% in others. At the same time exogenous MCC or GNG precursor infusion may be adjusted to maintain arterial blood [lactate] in the range of 1-2 mM (vide supra). Parenteral nutrition will eventually be stopped when enteral nutritional delivery is adequate, but the intravascular $Na^+$-L-(+)-Lactate infusion can be maintained or restarted if the patient's BES indicates a need to supplement enteral nutrition to achieve approximately the desired % GNG, or if the clinician decides to augment cerebral nutrition or to manage ICP.

In one embodiment, the invention shall commence intravascular infusion of $Na^+$-L-(+)-Lactate at the rate of 3 mg/kg/min plus parenteral (intravascular) nutritive support according to the AMDRs and TEE estimates as given by the IOM. In the absence of data on % GNG, the MCC or alternate embodiment infusion rate of approximately 3 mg/kg/min will continue until periodic blood sampling indicates that blood [lactate] reaches 4 mM, at which time the infusion rate will be maintained or adjusted up or down to maintain blood [lactate] at the target level.

When % GNG data become available, the combination of enteral and parenteral nutrition will be maintained or adjusted to achieve the target of GNG at which time exogenous MCC or GNG precursor infusion rate can be adjusted to maintain arterial blood [lactate] in the range of 1-2 mM (vide supra). Parenteral nutrition eventually may be stopped due to adequate enteral nutritional delivery, but the intravascular $Na^+$-L-(+)-Lactate infusion can be maintained or restarted if the patient's BES indicates a need to supplement enteral nutrition to achieve approximately 25% GNG, or if it is decided to augment cerebral nutrition or to manage ICP.

In one embodiment, the invention shall commence intravascular infusion of $Na^+$-L-(+)-Lactate, MCC or GNG precursor at the rate of 3 mg/kg/min plus parenteral (intravascular) nutritive support according to the AMDRs and TEE estimates as given by the Harris-Benedict equations. In the absence of data on % GNG, the MCC or alternate embodiment infusion rate of approximately 3 mg/kg/min will continue until periodic blood sampling indicates that blood [lactate] reaches 4 mM, at which time the infusion rate will be maintained or adjusted up or down to maintain blood [lactate] at the target level. When % GNG data become available, the combination of enteral and parenteral nutrition will be maintained or adjusted to achieve the target of 25% GNG at which time exogenous MCC or GNG precursor infusion rate can be adjusted to maintain arterial blood [lactate] in the range of 1-2 mM (vide supra). Parenteral nutrition may eventually be stopped due to adequate enteral nutritional delivery, but the intravascular $Na^+$-L-(+)-Lactate can be maintained or restarted if the patient's BES indicates a need to supplement enteral nutrition to achieve approximately 25% GNG, or if it is decided to augment cerebral nutrition or to manage ICP.

In a preferred embodiment, nutritive support treatment targets are 15-35% GNG or 20-25% GNG. In this embodiment, plasma [lactate] is targeted at 4 mM. In another preferred embodiment plasma [glucose] is targeted as 5-7 mM. These targets can be achieved by adjusting enteral and parenteral administration rates either singularly, or in combination. However, when % GNG is unknown, in addition to adjusting MCC, enteral and parenteral administration rates, Dextrose and/or insulin therapy may be indicated above a certain [glucose] such as 7.8, or below 5.6 mM. Rates of infusion of Dextrose should not exceed the endogenous glucose Rd (2-3 mg/kg/min) as this will cause a hyperglycemic condition.

Nutritive Support For Those Engaged in Physical Activity

To this point the invention as described pertains to the care of ill and injured individuals whose metabolism while significantly affected by disease states, approximates those of resting individuals. However, the methods and formulations described above are relevant to supporting BES of other individuals, such as those with hypermetabolic states such as athletes, soldiers and manual laborers engaged in strenuous physical activity. In athletic arenas, pools and stadia, in combat zones, and in the factory or on the farm individuals can increase metabolic rates 20-30 fold over rest. Importantly, during moderate to high-intensity exercise, carbohydrate energy sources (muscle glycogen, blood lactate, liver glycogen and blood glucose) are the predominant energy sources (103).

On such occasions, metabolic rate greatly exceeds that of the ill and injured, but it is neither possible to estimate BES by taking blood to measure % GNG, nor is it possible to come close to matching energy flux by supplying parenteral or enteral nutrition alone or in combination. Further, attempts to buttress BES by intravascular infusion of energy-containing formulations is either impractical, against rules of competition, or both. None the less, the formulations described herein, and the rates of oral consumption of those formulations can be efficacious in reducing the energy deficit of strenuous exercise, preserving limited glycogen an blood glucose reserves, compensating for dehydration and salt losses in sweating, controlling the effects of hyperthermia in hot an humid environments, reducing the perception of exertion, and thus prolonging the duration of activities such as exercise, warfare or work.

Again, with reference to the stresses imposed on athletes as an example, energy flux may increase more than an order of magnitude at a time when the capacity for enteral nutrient delivery is limited not by access to fluids and solid foods, but by gastric emptying and intestinal absorption. With regard to the fueling of athletes, the prime example being professional male cyclists, with single component drinks {e.g., 100% glucose (i.e., dextrose)}, the rates of gastric emptying and intestinal absorption approximate 1 g/min when the solute concentration is 6 g % (6 g/100 ml or 60 g/1,000 ml) when consumed at the rate of ≈1,000 ml/hr. However, if the solution consumed contains two sugar forms, such as glucose and fructose, the solute absorption rate can increase resulting in greater oxidation (109, 110). Interestingly, in terms of lactate shuttle theory, it is apparent that nutrient supplementation with glucose plus fructose increases lactate availability (1, 109, 110). Moreover, if the drink consumed contains multiple carbohydrate forms, the total carbohydrate (CHO) absorption rate, and physical performance can rise still further (1).

Reasons for the advantage of multiple, as opposed to single CHO form availability in sports drinks is attributable to several factors, but primarily the expression of multiple transport (carrier) proteins in the intestinal wall is primarily important. Expressed in the intestinal mucosa are transporters for lactate, glucose, fructose, acetate, and amino acids, among others. Further, some transporters are symporters, also called symports, meaning that they cotransport other substances, in the instance of lactate and glucose transporters, the co-transported moiety is sodium ion ($Na^+$). The presence of sodium-mediated symports is efficacious in terms of energy, electrolyte and water absorption.

These intestinal transporters accomplish what is termed the facilitated transport of solutes. This means that cellular energy sources such as adenosine triphosphate ("ATP") are not used, but viewed in three dimensions transporters are structured in such a way as to form channels, specific for the particular metabolite, that can move down a concentration gradient from intestine to portal blood. While not properly classed as enzymes, transporters display Michaelis-Menten kinetics, meaning that their transport capability possesses unique characteristics such as sensitivity to [substrate], (kM), and maximal rate of substrate transport (Vmax). Another key feature of transporters is that they demonstrate the characteristic termed saturation, where no further increase in transport despite increased solute availability once Vmax is achieved. Hence, because of the abundance of multiple intestinal solute transporters, each functioning independently, but sensitive to saturation by their respective substrates, by including more different forms of solutes as opposed to more of one single solute, a higher total rate of solute transport from intestinal lumen to portal blood can be accomplished.

Another feature of intestinal transporters relates to the facilitated transport of water through water channels, termed aquaporins, meaning water pores. Aquaporins facilitate the movement of water down concentration gradients. Alternatively stated, water follows the solutes, in other words, water moves to minimize the osmotic pressure differences exerted by solutes in different exchangeable compartments, such as between the intestinal lumen and portal blood. Restated another way, the transport of more carbohydrate energy forms move more $Na^+$ ions, and more water follows. Hence, sports drinks containing sub-saturating levels of multiple carbohydrate and amino acid energy forms move more energy, fluid and electrolytes than do single or dual solute-containing sports drinks.

To support BES in the injured and ill persons above we described parenteral and enteral fluid formulations containing lactate salts, esters and polymers (e.g., $Na^+$-lactate, arginyl-lactate, glycerol tri-lactate), glycerol tri-acetate, hexoses (glucose and fructose), disaccharides such as sucrose (glucose+fructose), maltodextrins (glucose polymers) and amino acids. Also described above are methods to deliver formulations to the ill or injured based on feedback from measurements of % GNG. Herein we also describe methods to deliver formulations to the ill and injured based on feedback knowledge of blood [lactate], e.g., 4 mM. Now also, we describe that those same formulations, or variations thereof, can be administered to those engaged in very high rates of energy expenditure, perhaps in challenging environments when measurements of BES using $D_2O$ or blood [metabolite] are not feasible or appropriate. In such case the solutions can be formulated in 6-8% (w/v) solutions that are consumed intermittently and as required due to the intensity of exercise or exertion, e.g., at the rate of 250 ml/15 mM, or 1,000 ml/hr to deliver fuel at a rate 1 g/min along with electrolytes and water. As such, a sports drink prescription or protocol would enable the individual to alter the consumption of the energy drink based on the type and intensity of activity performed.

In an ideal formulation, a sports drink would contain energy substrates, electrolytes and water sufficient to support needs for those substances in an athlete or other person engaged in strenuous exercise, perhaps in a stressful environment. Using already described formulations (vide supra) so that an 8% solution could contain: Sanguisal {$Na^+$-, $K^+$-, $Ca^{++}$-, $Mg^{++}$-L-(+)-lactate, and $NaH_2PO_4^-$} in the ratio of about 145, 4, 2.5, 1.5, and 1.0, In this iteration of formulation, Sanguisal would provide electrolytes ($Na^+$, $K^+$, $Ca^{++}$, $Mg^{++}$, and $H_2PO_4^-$) as well as energy substrate (lactate). Additionally, multiple additional substrates (arginyl-lactate, dextrose, fructose, sucrose, maltodextrin and amino acids in addition to arginine (e.g., glycine, alanine, glutamate, glutamine, leucine, isoleucine and valine) could be provided alone, or in combination in the formulation to be consumed orally. Within the domain of oral (enteral) supplementation, the formulation could include fructose and maltodextrins (glucose polymers) that are not appropriate for vascular infusion.

As an example of an 8% (w/v) sports drink formulation, the drink could consist of: 0.17% Sanguisal, 1.00% arginyl lactate and/or glycerol tri-lactate, 2.40% dextrose, 2.43% maltodextrin, and 2.00% fructose. Within the example provided, but maintaining the 8% solute content, changes in the relative contributions of each ingredient would be efficacious to the extent that additions of other amendments such as glycerol tri-acetate (GTA), alanine, branched chain and other amino acids are possible, determined largely by the science of utilizing multiple energy substrates that would be transported by specific intestinal transporters, but also by the availability of ingredients and to make beverages flavorful. For example, the components of dextrose and maltodextrins could be combined to provide 4.8% of either; the fructose and dextrose components could be combined to provide 4.4% of total as sucrose (cane or beet sugar), and the Sanguisal, arginyl-lactate plus GTL and GTA component could be combined to provide 1.0-2.0% of either. Similarly, the inclusion of alanine, branched chain and other amino acids to the level of 1%, would result in systematic reductions in the concentrations of other amendments keeping the total solute content at about 8% (w/v).

As an example of the sports drink "prescription" the suggested consumption of the energy drink would be >1 g/min at the highest intensity, but at 50% of maximal workload (e.g., brisk walking) the consumption would be 0.5 g/min.

Administering/drinking of oral sports drink can be done with the measurement of blood [lactate] using a concentration meter and a small blood sample to monitor blood [lactate] during training. An individual could use the measurement of blood [lactate] at rest and during exercise to augment the formulations and consumption of the sports drinks depending on training goals and type of activity. For example, by raising blood lactate concentration during exercise by 0.5 to 1.0 mM by the consumption of lactate- or fructose-containing beverages (109, 110), and thereby conserving endogenous carbohydrate stores, performance may be improved (speed, endurance, duration, among other measure) (1). Alternatively, and analogous to the use of a hyperinsulinemic-euglycemic glucose clamp to assess insulin action in a diabetic, it is possible to use a 4 mM LC procedure to assess lactate clearance capacity in a resting athlete before and after training.

In summary, although the energy and fluid needs of athletes, manual laborers and soldiers in combat can exceed the rate of food energy and fluid resupply rates imposed by the constraints of gastric emptying and intestinal absorption, oral formulations can support BES by supplying at least some to the fuel and electrolytes that can be relatively rapidly assimilated. Lactate-containing and other GNG precursor or MCC drinks offer the advantage of providing oxidizable fuel most rapidly (1, 104). As well, because lactate is a major gluconeogenic precursor (24, 54, 113), lactate in a sport drink will indirectly support blood glucose homeostasis during hard exercise by providing substrate for GNG and reducing liver and muscle GLY. Additionally, as the salt of an acid, lactate anion is a buffer. Providing dextrose in a sports drink will directly support blood glucose homeostasis and help minimize hepatic GLY. The presence of lactate and glucose in sports drinks is efficacious also because they ate transported by symporters that also move sodium ion from intestinal lumen into the portal circulation. Providing fructose in a sports drink is efficacious as it is flavorful, and also gives rise to hepatic glucose and lactate production.

Providing acetate in a sports drink is efficacious because of the abundance of intestinal transporters and because acetate is rapidly oxidized, thus sparing glucose, glycogen sources. Providing branched-chain amino acids ("BCAA"), such as leucine, in small amounts a sports drink is efficacious because BCAAs are transported independently and are oxidized during exercise. Providing the amino acid arginine in a sports drink is efficacious because it can be used as a lactate carrier and a precursor to nitric oxide (NO), a vasodilator. Providing glycerol in the form of GTL and GTA in a sports drink is efficacious because it can be used as a carrier for lactate and acetate, and because glycerol is a gluconeogenic precursor. Thus, acting individually, but more effectively in concert, multiple amendments in sports drinks act to reduce the stress of exercise by providing fuel energy, fluid and electrolytes to increase endurance capacity by extending the time of exercise, particularly at high power outputs (1).

With regard to the present invention, the many features and advantages of the present invention are apparent from the written description, and thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

Various elements of the invention are described as modules implemented as software on a general purpose computer and others as hardware elements. It should be apparent that in various embodiments of the invention, implementation of software can be executed by embedded hardware, or vice versa, or in some combination of software and hardware. Also, a computer may take the form of an integrated circuit, printed circuit board, handheld computer, or any general-purpose computer without limitation.

Part of the invention may be implemented by a general-purpose computer, embedded circuitry, or some combination of these. The software execution may be accomplished through the use of a program storage device readable by the computer and encoding a program of instructions executable by the computer for performing the operations described above. The program storage device may take the form of any memory known in the art or subsequently developed. The program of instructions may be object code, i.e., in binary form that is executable more-or-less directly by the computer; in source code that requires compilation or interpretation before execution; or in some intermediate form such as partially compiled code and/or a collection of executable library files. The precise forms of the program storage device and of the encoding of instructions are immaterial here.

The invention also contemplates use of computer networks known in the art, including but not limited to, intranets such as corporate networks, local and wide area networks, the Internet and the World Wide Web. Wire and wireless communication and communication protocols known in the art, such as, but not limited to, radio, infrared, Bluetooth, Ethernet and other wireless and wired networks, are also contemplated.

Preferred embodiments of flow direction between elements, looping and iteration are discussed, but alternative embodiments of these flows are contemplated by the invention. Any elements or other features described in the figures, even if not described in the specification, are supported in the figures so as to be enabling. All references cited here are incorporated in their entirety for all purposes.

REFERENCES

1. Azevedo J L, Tietz E, Two-Feathers T, Paull J, and Chapman K. Lactate, fructose and glucose oxidation profiles in sports drinks and the effect on exercise performance. *PLoS One* 2: e927, 2007.
2. Bergman B C, Butterfield G E, Wolfel E E, Lopaschuk G D, Casazza G A, Horning M A, and Brooks G A. Muscle net glucose uptake and glucose kinetics after endurance training in men. *Am J Physiol* 277: E81-92, 1999.
3. Bergman B C, Horning M A, Casazza G A, Wolfel E E, Butterfield G E, and Brooks G A. Endurance training increases gluconeogenesis during rest and exercise in men. *Am J Physiol Endocrinol Metab* 278: E244-251, 2000.
4. Bergman B C, Wolfel E E, Butterfield G E, Lopaschuk G D, Casazza G A, Horning M A, and Brooks G A. Active muscle and whole body lactate kinetics after endurance training in men. *Journal of applied physiology* 87: 1684-1696, 1999.
5. Brooks G A. Cell-cell and intracellular lactate shuttles. *Journal of Physiology* 587: 5591-5600, 2009.
6. Brooks G A. Glycolytic end product and oxidative substrate during sustained exercise in mammals—the "lactate shuttle. *Comparative Physiology and Biochemistry—Current Topics and Trends, Volume A, Respiration—Metabolism—Circulation:* 208-218, 1984.
7. Brooks G A. Lactate Shuttles in Nature. *Biochemical Society Transactions* 30: 258-264, 2002.
8. Brooks G A, Butte N F, Rand W M, Flatt J P, and Caballero B. Chronicle of the Institute of Medicine physical activity recommendation: how a physical activity recommendation came to be among dietary recommendations. *Am J Clin Nutr* 79: 921S-930S, 2004.
9. Brooks G A, Butterfield G E, Wolfe R R, Groves B M, Mazzeo R S, Sutton J R, Wolfel E E, and Reeves J T. Decreased reliance on lactate during exercise after acclimatization to 4,300 m. *Journal of applied physiology* 71: 333-341, 1991.
10. Brooks G A, Butterfield G E, Wolfe R R, Groves B M, Mazzeo R S, Sutton J R, Wolfel E E, and Reeves J T. Increased dependence on blood glucose after acclimatization to 4,300 m. *Journal of applied physiology* 70: 919-927, 1991.
11. Brooks G A and Donovan C M. Effect of endurance training on glucose kinetics during exercise. *Am J Physiol* 244: E505-512, 1983.
12. Brooks G A, Fahey T D, and Baldwin K M. Exercise Physiology: Human Bioenergetics and It's Applications. McGraw-Hill, 2004, p. 162-171, 753-756.
13. Brooks G A, Wolfel E E, Butterfield G E, Cymerman A, Roberts A C, Mazzeo R S, and Reeves J T. Poor relationship between arterial [lactate] and leg net release during exercise at 4,300 m altitude. *Am J Physiol* 275: R1192-1201, 1998.
14. Brooks G A, Wolfel E E, Groves B M, Bender P R, Butterfield G E, Cymerman A, Mazzeo R S, Sutton J R, Wolfe R R, and Reeves J T. Muscle accounts for glucose disposal but not blood lactate appearance during exercise after acclimatization to 4,300 m. *Journal of applied physiology* 72: 2435-2445, 1992.
15. Bullock R, Chesnut R M, Clifton G, Ghajar J, Marion D W, Narayan R K, Newell D W, Pitts L H, Rosner M J, and Wilberger J W. Guidelines for the management of severe head injury. Brain Trauma Foundation. *Eur J Emerg Med* 3: 109-127, 1996.
16. Cahill G J, Jr., Owen O E, and Morgan A P. The consumption of fuels during prolonged starvation. *Adv Enzyme Regul* 6: 143-150, 1968.
17. Cannon W B. The Wisdom of the Body. New York: Norton, 1932.
18. Casaer M P, Hermans G, Wilmer A, and Van den Berghe G. Impact of early parenteral nutrition completing enteral nutrition in adult critically ill patients (EPaNIC trial): a study protocol and statistical analysis plan for a randomized controlled trial. *Trials* 12: 21, 2011.
19. Chacko S K, Ordonez J, Sauer P J, and Sunehag A L. Gluconeogenesis is not regulated by either glucose or insulin in extremely low birth weight infants receiving total parenteral nutrition. *J Pediatr* 158: 891-896, 2011.
20. Chacko S K, Sunehag A L, Sharma S, Sauer P J, and Haymond M W. Measurement of gluconeogenesis using glucose fragments and mass spectrometry after ingestion of deuterium oxide. *Journal of applied physiology* 104: 944-951, 2008.
21. Colberg S R, Casazza G A, Horning M A, and Brooks G A. Increased dependence on blood glucose in smokers during rest and sustained exercise. *Journal of Applied Physiology* 76: 26-32, 1994.
22. Colberg S R, Casazza G A, Horning M A, and Brooks G A. Metabolite and hormonal response in smokers during rest and sustained exercise. *Med Sci Sports Exerc* 27: 1527-1534, 1995.
23. Donovan C M and Brooks G A. Endurance training affects lactate clearance, not lactate production. *Am J Physiol* 244: E83-92, 1983.
24. Emhoff C A, Messonnier L A, Horning M A, Fattor J A, Carlson T J, and Brooks G A. Gluconeogenesis and hepatic glycogenolysis during exercise at the lactate threshold. *Journal of Applied Physiology* 114: 297-306, 2013.
25. Fahey T D, Larsen J D, Brooks G A, Colvin W, Henderson S, and Lary D. The effects of ingesting poly-lactate or glucose polymer drinks during prolonged exercise. *Int J Sport Nutr* 1: 249-256, 1991.
26. Friedlander A L, Casazza G A, Horning M A, Huie M J, and Brooks G A. Training-induced alterations of glucose flux in men. *Journal of applied physiology* 82: 1360-1369, 1997.
27. Friedlander A L, Casazza G A, Horning M A, Huie M J, Piacentini M F, Trimmer J K, and Brooks G A. Training-induced alterations of carbohydrate metabolism in women: women respond differently from men. *Journal of applied physiology* 85: 1175-1186, 1998.
28. Glenn T C, Kelly D F, Boscardin W J, McArthur D L, Vespa P, Oertel M, Hovda D A, Bergsneider M, Hillered L, and Martin N A. Energy dysfunction as a predictor of outcome after moderate or severe head injury: indices of oxygen, glucose, and lactate metabolism. *J Cereb Blood Flow Metab* 23: 1239-1250, 2003.
29. Griffiths R D. Too much of a good thing: the curse of overfeeding. *Crit Care* 11: 176, 2007.
30. Guo Z K, Lee W N, Katz J, and Bergner A E. Quantitation of positional isomers of deuterium-labeled glucose by gas chromatography/mass spectrometry. *Anal Biochem* 204: 273-282, 1992.

31. Hachey D L, Wong W W, Boutton T W, and, and Klein P D. Isotope ratio measurements in nutrition and biomedical research. *Mass Spectrom Rev* 6: 289-328, 1987.
32. Harris J A and Benedict F G. A Biometric Study of Human Basal Metabolism. *Proc Natl Acad Sci USA* 4: 370-373, 1918.
33. Hashimoto T, Hussien R, Cho H S, Kaufer D, and Brooks G A. Evidence for the mitochondrial lactate oxidation complex in rat neurons: demonstration of an essential component of brain lactate shuttles. *PLoS One* 3: e2915, 2008.
34. Haymond M W and Sunehag A L. The reciprocal pool model for the measurement of gluconeogenesis by use of [U-(13)C]glucose. *Am J Physiol Endocrinol Metab* 278: E140-145, 2000.
35. Hellerstein M K, Neese R A, Linfoot P, Christiansen M, Turner S, and Letscher A. Hepatic gluconeogenic fluxes and glycogen turnover during fasting in humans. A stable isotope study. *J Clin Invest* 100: 1305-1319, 1997.
36. Henderson G C, Horning M A, Wallis G A, and Brooks G A. Pyruvate metabolism in working human skeletal muscle. *Am J Physiol Endocrinol Metab* 292: E366, 2007.
37. Hetenyi G, Jr. Correction for the metabolic exchange of 14C for 12C atoms in the pathway of gluconeogenesis in vivo. *Fed Proc* 41: 104-109, 1982.
38. Hetenyi G, Jr. Gluconeogenesis in vivo. *Am J Physiol* 249: R792-793, 1985.
39. Huie M J, Casazza G A, Horning M A, and Brooks G A. Smoking increases conversion of lactate to glucose during submaximal exercise. *Journal of applied physiology* 80: 1554-1559, 1996.
40. Jenssen T, Nurjhan N, Consoli A, and Gerich J E. Dose-response effects of lactate infusions on gluconeogenesis from lactate in normal man. *Eur J Clin Invest* 23: 448-454, 1993.
41. Johnson M L, Hussien R, Horning M A, and Brooks G A. Transpulmonary pyruvate kinetics. *Am J Physiol Regul Integr Comp Physiol* 301: R769-774, 2011.
42. Junghans P, Gors S, Lang I S, Steinhoff J, Hammon H M, and Metges C C. A simplified mass isotopomer approach to estimate gluconeogenesis rate in vivo using deuterium oxide. *Rapid Commun Mass Spectrom* 24: 1287-1295, 2010.
43. Kalhan S C, Parimi P, Van Beek R, Gilfillan C, Saker F, Gruca L, and Sauer P J. Estimation of gluconeogenesis in newborn infants. *Am J Physiol Endocrinol Metab* 281: E991-997, 2001.
44. Landau B R. Quantifying the contribution of gluconeogenesis to glucose production in fasted human subjects using stable isotopes. *Proc Nutr Soc* 58: 963-972, 1999.
45. Landau B R, Wahren J, Chandramouli V, Schumann W C, Ekberg K, and Kalhan S C. Use of 2H2O for estimating rates of gluconeogenesis. Application to the fasted state. *J Clin Invest* 95: 172-178, 1995.
46. Lanza I R, Zhang S, Ward L E, Karakelides H, Raftery D, and Nair K S. Quantitative metabolomics by H-NMR and LC-MS/MS confirms altered metabolic pathways in diabetes. *PLoS One* 5: e10538, 2010.
47. Loh N H W and Griffiths R D. *The Curse of Overfeeding and the Blight of Underfeeding*: Springer New York, 2009.
48. Mallet R T and Sun J. Antioxidant properties of myocardial fuels. *Mol Cell Biochem* 253: 103-111, 2003.
49. Mathews T J and MacDorman M F. Infant mortality statistics from the 2007 period linked birth/infant death data set. *Natl Vital Stat Rep* 59: 1-30, 2011.
50. McClave S A, Lowen C C, Kleber M J, Nicholson J F, Jimmerson S C, McConnell J W, and Jung L Y. Are patients fed appropriately according to their caloric requirements? *JPEN J Parenter Enteral Nutr* 22: 375-381, 1998.
51. Medicine I O. DIETARY REFERENCE INTAKES: Energy, Carbohydrate, Fiber, Fat, Fatty Acids, Cholesterol, Protein, and Amino Acids. Washington, D.C.: The National Academies Press, 2005, p. 107-264.
52. Messonnier A L, Emhoff C W, Fattor J A, Horning M A, T. J. C, and Brooks G A. Lactate kinetics at the lactate threshold in trained and untrained men. *Journal of Applied Physiology* 114, 2013.
53. Messonnier L, Samb A, Tripette J, Gogh B D, Loko G, Sall N D, Feasson L, Hue O, Lamothe S, Bogui P, and Connes P. Moderate endurance exercise is not a risk for rhabdomyolysis or renal failure in sickle cell trait carriers. *Clin Hemorheol Microcirc* 51: 193-202, 2012.
54. Meyer C, Dostou J M, Welle S L, and Gerich J E. Role of human liver, kidney, and skeletal muscle in postprandial glucose homeostasis. *Am J Physiol Endocrinol Metab* 282: E419-427, 2002.
55. Miller B F, Fattor J A, Jacobs K A, Horning M A, Navazio F, Lindinger M I, and Brooks G A. Lactate and glucose interactions during rest and exercise in men: effect of exogenous lactate infusion. *J Physiol* 544: 963-975, 2002.
56. Miller B F, Fattor J A, Jacobs K A, Horning M A, Suh S H, Navazio F, and Brooks G A. Metabolic and cardiorespiratory responses to "the lactate clamp". *Am J Physiol Endocrinol Metab* 283: E889-898, 2002.
57. Miller B F, Lindinger M I, Fattor J A, Jacobs K A, Leblanc P J, Duong M, Heigenhauser G J, and Brooks G A. Hematological and acid-base changes in men during prolonged exercise with and without sodium-lactate infusion. *Journal of applied physiology* 98: 856-865, 2005.
58. Neese R A, Schwarz J M, Faix D, Turner S, Letscher A, Vu D, and Hellerstein M K. Gluconeogenesis and intrahepatic triose phosphate flux in response to fasting or substrate loads. Application of the mass isotopomer distribution analysis technique with testing of assumptions and potential problems. *J Biol Chem* 270: 14452-14466, 1995.
59. Peter J V, Moran J L, and Phillips-Hughes J. A meta-analysis of treatment outcomes of early enteral versus early parenteral nutrition in hospitalized patients. *Crit Care Med* 33: 213-220; discussion 260-211, 2005.
60. Phillips S M. Dietary protein requirements and adaptive advantages in athletes. *Br J Nutr* 108 Suppl 2: S158-167, 2012.
61. Ryou M G, Flaherty D C, Hoxha B, Gurji H, Sun J, Hodge L M, Olivencia-Yurvati A H, and Mallet R T. Pyruvate-enriched cardioplegia suppresses cardiopulmonary bypass-induced myocardial inflammation. *Ann Thorac Surg* 90: 1529-1535, 2010.
62. Ryou M G, Flaherty D C, Hoxha B, Sun J, Gurji H, Rodriguez S, Bell G, Olivencia-Yurvati A H, and Mallet R T. Pyruvate-fortified cardioplegia evokes myocardial erythropoietin signaling in swine undergoing cardiopulmonary bypass. *Am J Physiol Heart Circ Physiol* 297: H1914-1922, 2009.
63. Ryou M G, Liu R, Ren M, Sun J, Mallet R T, and Yang S H. Pyruvate protects the brain against ischemia-reperfusion injury by activating the erythropoietin signaling pathway. *Stroke* 43: 1101-1107, 2012.

64. Schurr A. Lactate: a major and crucial player in normal function of both muscle and brain. *J Physiol* 586: 2665-2666, 2008.
65. Schwarz J M, Chiolero R, Revelly J P, Cayeux C, Schneiter P, Jequier E, Chen T, and Tappy L. Effects of enteral carbohydrates on de novo lipogenesis in critically ill patients. *Am J Clin Nutr* 72: 940-945, 2000.
66. Scrimgeour C M, Rollo M M, Mudambo S M, Handley L L, and Prosser S J. A simplified method for deuterium/hydrogen isotope ratio measurements on water samples of biological origin. *Biol Mass Spectrom* 22: 383-387, 1993.
67. Selye H. Stress and the general adaptation syndrome. *Br Med J* 1: 1383-1392, 1950.
68. Sharma A B, Barlow M A, Yang S H, Simpkins J W, and Mallet R T. Pyruvate enhances neurological recovery following cardiopulmonary arrest and resuscitation. *Resuscitation* 76: 108-119, 2008.
69. Sharma A B, Knott E M, Bi J, Martinez R R, Sun J, and Mallet R T. Pyruvate improves cardiac electromechanical and metabolic recovery from cardiopulmonary arrest and resuscitation. *Resuscitation* 66: 71-81, 2005.
70. Slone D S. Nutritional support of the critically ill and injured patient. *Crit Care Clin* 20: 135-157, 2004.
71. Smith D, Pernet A, Hallett W A, Bingham E, Marsden P K, and Amiel S A. Lactate: a preferred fuel for human brain metabolism in vivo. *J Cereb Blood Flow Metab* 23: 658-664, 2003.
72. Tayek J A and Katz J. Glucose production, recycling, and gluconeogenesis in normals and diabetics: a mass isotopomer [U-13C]glucose study. *Am J Physiol* 270: E709-717, 1996.
73. Trimmer J K, Casazza G A, Horning M A, and Brooks G A. Autoregulation of glucose production in men with a glycerol load during rest and exercise. *Am J Physiol Endocrinol Metab* 280: E657-668, 2001.
74. Trimmer J K, Schwarz J M, Casazza G A, Horning M A, Rodriguez N, and Brooks G A. Measurement of gluconeogenesis in exercising men by mass isotopomer distribution analysis. *Journal of applied physiology* 93: 233-241, 2002.
75. Umpierrez G E, Hellman R, Korytkowski M T, Kosiborod M, Maynard G A, Montori V M, Seley J J, and Van den Berghe G. Management of hyperglycemia in hospitalized patients in non-critical care setting: an endocrine society clinical practice guideline. *J Clin Endocrinol Metab* 97: 16-38, 2012.
76. van Rosendal S P, Osborne M A, Fassett R G, and Coombes J S. Guidelines for glycerol use in hyperhydration and rehydration associated with exercise. *Sports Med* 40: 113-129, 2010.
77. Verbruggen S C, de Betue C T, Schierbeek H, Chacko S, van Adrichem L N, Verhoeven J, van Goudoever J B, and Joosten K F. Reducing glucose infusion safely prevents hyperglycemia in post-surgical children. *Clin Nutr* 30: 786-792, 2011.
78. Vespa P, Boonyaputthikul R, McArthur D L, Miller C, Etchepare M, Bergsneider M, Glenn T, Martin N, and Hovda D. Intensive insulin therapy reduces microdialysis glucose values without altering glucose utilization or improving the lactate/pyruvate ratio after traumatic brain injury. *Crit Care Med* 34: 850-856, 2006.
79. Widmaier E P, Raff H, and Strang K T. Vander's Human Physiology. (12th ed.). New York: McGraw-Hill, 2011, p. 528-530, Back inside cover.
80. Wolfe R R. Radioactive and Stable Isotope Tracers in Biomedicine: Principles and Practice of Kinetic Analysis. New York: Wiley-Liss, 1982, p. 81-83, 142-143.
81. Yang D, Diraison F, Beylot M, Brunengraber D Z, Samols M A, Anderson V E, and Brunengraber H. Assay of low deuterium enrichment of water by isotopic exchange with [U-13C3]acetone and gas chromatography-mass spectrometry. *Anal Biochem* 258: 315-321, 1998.
82. Yarandi S S, Zhao V M, Hebbar G, and Ziegler T R. Amino acid composition in parenteral nutrition: what is the evidence? *Curr Opin Clin Nutr Metab Care* 14: 75-82, 2011.
83. Zhang Y and Szolovits P. Patient-specific learning in real time for adaptive monitoring in critical care. *J Biomed Inform* 41: 452-460, 2008.
84. Zilversmit D B, Entenman C, Fishier M C, and Chaikoff I L. The Turnover Rate of Phospholipids in the Plasma of the Dog as Measured with Radioactive Phosphorus. *J Gen Physiol* 26: 333-340, 1943.

Additional References (note there are no references 85-100)

101. Bratton S L, Chestnut R M, Ghajar J, McConnell Hammond F F, Harris O A, Hartl R, Manley G T, Nemecek A, Newell D W, Rosenthal G, Schouten J, Shutter L, Timmons S D, Ullman J S, Videtta W, Wilberger J E, and Wright D W. Guidelines for the management of severe traumatic brain injury. I. Blood pressure and oxygenation. *J Neurotrauma* 24 Suppl 1: S7-13, 2007.
102. Brooks G A. Anaerobic threshold: review of the concept and directions for future research. *Med Sci Sports Exerc* 17: 22-34, 1985.
103. Brooks G A and Mercier J. Balance of carbohydrate and lipid utilization during exercise: the "crossover" concept. *Journal of applied physiology* 76: 2253-2261, 1994.
104. Emhoff C A, Messonnier L A, Horning M A, Fattor J A, Carlson T J, and Brooks G A. Direct and indirect lactate oxidation in trained and untrained men. *Journal of Applied Physiology*, 115: 829-838, 2013.
105. Gallagher C N, Carpenter K L, Grice P, Howe D J, Mason A, Timofeev I, Menon D K, Kirkpatrick P J, Pickard J D, Sutherland G R, and Hutchinson P J. The human brain utilizes lactate via the tricarboxylic acid cycle: a 13C-labelled microdialysis and high-resolution nuclear magnetic resonance study. *Brain* 132: 2839-2849, 2009.
106. Gohil K and Brooks G A. Exercise tames the wild side of the Myc network: a hypothesis. *Am J Physiol Endocrinol Metab* 303: E18-30, 2012.
107. Hill A V and Lupton H. Muscular exercise, lactic acid and the supply and utilization of oxygen. *Quar J Med* 16: 135-171, 1923.
108. Ichai C, Armando G, Orban J C, Berthier F, Rami L, Samat-Long C, Grimaud D, and Leverve X. Sodium lactate versus mannitol in the treatment of intracranial hypertensive episodes in severe traumatic brain-injured patients. *Intensive Care Med* 35: 471-479, 2009.
109. Jeukendrup A E, Moseley L, Mainwaring G I, Samuels S, Perry S, and Mann C H. Exogenous carbohydrate oxidation during ultraendurance exercise. *Journal of Applied Physiology* 100: 1134-1141, 2006.
110. Lecoultre V, Benoit R, Carrel G, Schutz Y, Millet G P, Tappy L, and Schneiter P. Fructose and glucose co-ingestion during prolonged exercise increases lactate and glucose fluxes and oxidation compared with an equimolar intake of glucose. *Am J Clin Nutr* 92: 1071-1079, 2010
111. Margaria R., Edwards H. T. a, and Dill D B. The possible mechanisms of contracting and paying the oxygen debt and the role of Lactic Acid In Muscular Contraction. *Am J Physiol* 106: 689-715, 1933.
112. Mazzeo R S, Brooks G A, Schoeller D A, and Budinger T F. Disposal of blood [1-13C]lactate in humans during rest and exercise. *Journal of applied physiology* 60: 232-241, 1986.
113. Meyer C, Stumvoll M, Dostou J, Welle S, Haymond M, and Gerich J. Renal substrate exchange and gluconeogenesis in normal postabsorptive humans. *Am J Physiol Endocrinol Metab* 282: E428-434, 2002.
114. Meyerhof O. Die Energieumwandlungen im Muskel II. Das Schicksal der Milchsaure in der Erholungsperiode des Muskels. *Pflügers Archiv ges Physiol Mensch Tiere* 182: 284-317, 1920.
115. Pellerin L and Magistretti P J. Sweet sixteen for ANLS. *J Cereb Blood Flow Metab*, 2011.
116. Stanley W C, Gertz E W, Wisneski J A, Neese R A, Morris D L, and Brooks G A. Lactate extraction during net lactate release in legs of humans during exercise. *Journal of applied physiology* 60: 1116-1120, 1986.
117. Stanley W C, Wisneski J A, Gertz E W, Neese R A, and Brooks G A. Glucose and lactate interrelations during moderate-intensity exercise in humans. *Metabolism* 37: 850-858, 1988.
118. van Hall G, Stromstad M, Rasmussen P, Jans O, Zaar M, Gam C, Quistorff B, Secher N H, and Nielsen H B. Blood lactate is an important energy source for the human brain. *J Cereb Blood Flow Metab* 29: 1121-1129, 2009.

What is claimed is:

1. A method of providing nutritional support to a human patient that is unconscious or comatose, the method comprising:
    identifying a patient having a blood lactate concentration less than about 2.0 mM, wherein the patient is a human patient that is unconscious or comatose and wherein the identifying comprises:
    taking a blood sample from the patient;
    analyzing the blood sample with a lactate analyzer and determining that a blood lactate concentration of the patient is less than about 2.0 mM; and
    administering a nutritional support to the patient;
    wherein the nutritional support comprises a gluconeogenic precursor and/or a monocarboxylate compound and the administration is effective to achieve a blood lactate concentration greater than about 2.0 mM in the patient.

2. The method of claim 1 wherein the nutritional support comprises one or more salts.

3. The method of claim 1 wherein the nutritional support comprises a molecular label.

4. The method of claim 1 wherein the nutritional support has a milliosmolality of less than about 1000.

5. The method of claim 1 wherein the nutritional support comprises an amino acid.

6. The method of claim 1 wherein the nutritional support comprises one or more from the group consisting of: glycerol, glycerol tri-lactate, glycerol tri-acetate, arginyl lactate, lactate N-acetylcysteine ester, pyruvate, acetoacetate, and beta-hydroxy butyrate.

7. The method of claim 1 wherein the administration is further effective to modulate fractional gluconeogenesis in the patient.

8. The method of claim 1 wherein the administration is further effective to modulate blood glucose in the patient.

9. The method of claim 1 wherein the the administration is further effective to achieve a blood lactate to pyruvate ratio of at least about 10 in the patient.

10. A method of providing nutritional support to a human patient that is unconscious or comatose, the method comprising:
    identifying a patient having a blood lactate concentration less than about 2.0 mM, wherein the patient is a human patient that is unconscious or comatose and wherein the identifying comprises:
    taking a blood sample from the patient;
    analyzing the blood sample with a lactate analyzer and determining that a blood lactate concentration of the patient is less than about 2.0 mM;
    administering a nutritional support to the patient; wherein the nutritional support comprises a gluconeogenic precursor and/or a monocarboxylate compound and the administration is effective to achieve a blood lactate concentration greater than about 2.0 mM in the patient; and
    repeating the taking, analyzing, receiving and administering at least once.

11. The method of claim 10 wherein the nutritional support comprises one or more salts.

12. The method of claim 10 wherein the nutritional support comprises a molecular label.

13. The method of claim 10 wherein the nutritional support has a milliosmolality of less than about 1000.

14. The method of claim 10 wherein the nutritional support comprises an amino acid.

15. The method of claim 10 wherein the nutritional support comprises one or more from the group consisting of: glycerol, glycerol tri-lactate, glycerol tri-acetate, arginyl lactate, lactate N-acetylcysteine ester, pyruvate, acetoacetate, and beta-hydroxy butyrate.

16. The method of claim 10 wherein the administration is further effective to modulate fractional gluconeogenesis in the patient.

17. The method of claim 10 wherein the administration is further effective to modulate blood glucose in the patient.

18. The method of claim 10 wherein the the administration is further effective to achieve a blood lactate to pyruvate ratio of at least about 10 in the patient.

* * * * *